(12) United States Patent
Kuramata et al.

(10) Patent No.: US 7,412,088 B2
(45) Date of Patent: Aug. 12, 2008

(54) INSPECTION METHOD, AND INSPECTION DEVICE, AND MANUFACTURING FOR DISPLAY PANEL

(75) Inventors: Osamu Kuramata, Shiga (JP); Hiromichi Sasamoto, Kyoto (JP); Hiroki Sugihara, Shiga (JP); Keiji Tsuda, Shiga (JP)

(73) Assignee: Toray Industries, Inc. (JP)

( * ) Notice: Subject to any disclaimer, the term of this patent is extended or adjusted under 35 U.S.C. 154(b) by 759 days.

(21) Appl. No.: 10/469,618

(22) PCT Filed: Feb. 28, 2002

(86) PCT No.: PCT/JP02/01854

§ 371 (c)(1),
(2), (4) Date: Sep. 4, 2003

(87) PCT Pub. No.: WO02/071023

PCT Pub. Date: Sep. 12, 2002

(65) Prior Publication Data

US 2004/0135827 A1 Jul. 15, 2004

(30) Foreign Application Priority Data

Mar. 6, 2001 (JP) ............................ 2001-61759
Mar. 6, 2001 (JP) ............................ 2001-61760

(51) Int. Cl.
*G06K 9/00* (2006.01)

(52) U.S. Cl. .................. 382/141; 382/149; 324/770; 345/87; 345/904; 250/581; 348/180; 427/157

(58) Field of Classification Search ............... 382/141, 382/149; 324/770, 753, 754; 315/169.1; 349/102, 192, 149, 152, 54, 150; 345/30, 345/204, 60, 904, 87, 98; 348/92, 180; 250/584, 250/581, 484.4; 313/582; 427/8, 157; 445/59
See application file for complete search history.

(56) References Cited

U.S. PATENT DOCUMENTS

| | | | | |
|---|---|---|---|---|
| 4,759,033 A * | 7/1988 | Ariessohn | ................... | 374/161 |
| 5,663,005 A * | 9/1997 | Dooms et al. | ............... | 428/690 |
| 5,707,549 A * | 1/1998 | Matsukiyo et al. | .... | 252/301.4 R |
| 6,129,827 A * | 10/2000 | Nakazawa et al. | .......... | 204/508 |
| 6,656,608 B1 * | 12/2003 | Kita et al. | ................... | 428/690 |
| 6,831,995 B1 * | 12/2004 | Asano et al. | ................. | 382/141 |
| 2002/0009536 A1 * | 1/2002 | Iguchi et al. | ................... | 427/10 |
| 2002/0024498 A1 * | 2/2002 | Vos et al. | ..................... | 345/156 |

* cited by examiner

Primary Examiner—Sheela C Chawan
(74) Attorney, Agent, or Firm—DLA Piper US LLP

(57) ABSTRACT

A method of inspecting a display panel having a substrate and a plurality of fluorescent layers including measuring bright and dark signals reflected by the fluorescent layers while moving the substrate or an illuminating means generating the signals and an imaging means receiving the signals in a direction across the plurality of fluorescent layers at predetermined intervals, and measuring an application volume for each fluorescent layer from the signals obtained by the imaging means.

28 Claims, 30 Drawing Sheets

$P_0$
(Filling Volume V0)

P₁
(Filling Volume V1)

P$_2$
(Filling Volume V2)

P₃
(Filling Volume V3)

INSPECTION METHOD, AND INSPECTION DEVICE, AND MANUFACTURING FOR DISPLAY PANEL

TECHNICAL FIELD

The present invention relates to an inspection method for carrying out inspection of a pattern formed, in particular, on a substrate with high accuracy in a flat display panel represented by a liquid crystal display panel (hereinafter, referred to as "LCD") and a plasma display panel (hereinafter, referred to as "PDP").

BACKGROUND ART

In recent years, increase of the size of screens and decrease of the size of pixels of a spread display such as an LCD and a PDP have been advanced, and it is very difficult to manufacture non-defective products, and a serious problem occurs in ensuring the yield. Thus, it is a general practice of ensuring the yield by including inspections and repairs in a manufacturing step of the flat display panel to recondition a defective panel as a non-defective one.

In particular, in order to inspect the application state of liquid phosphor applied to a back plate of the PDP, the technology disclosed in, for example, Japanese Unexamined Patent Application Publication No. 2000-131226 is applicable. In this technology, the structure of a measurement surface can be inspected by allowing the light to be incident on the measurement surface of an object to be inspected by light, capturing the reflected light thereby, and measuring the change in intensity of the obtained reflected light.

When carrying out the above inspection using the light, various optical conditions must be optimized according to the structural characteristic of the object in order to increase the accuracy of the inspection. Specific optical conditions include the angle of incidence, the angle of reflection, the wavelength, the intensity, the scattering, and the polarizing direction of the light.

However, in the above conventional technology, any method for optimizing the optical conditions according to the structural characteristic of the object has not been demonstrated, and problems occur in that the shape of the pattern for forming the surface is changed by the change in a manufacturing condition of the object, and the accuracy of the inspection is considerably degraded or the inspection becomes impossible if the structural characteristic is different according to the stage of the manufacturing steps even with the products of the same kind.

The object of the present invention is to provide a method for solving the disadvantages of the above conventional technology, determining the optimum optical condition for the inspection of the surface shape by the structural characteristic of the object to be inspected, reflecting the determined condition in an inspection device to carry out the inspection with high accuracy, improving the yield without degrading the yield rate, and manufacturing a substrate of high quality and high reliability.

DISCLOSURE OF INVENTION

In order to achieve the above objects, an inspection method, and inspection device and a manufacturing method of a display panel of the present invention have the configuration described below.

An inspection method of a display panel of the present invention is characterized in that an illuminating means, an imaging means, and a signal processing means are provided, bright and dark signals of fluorescent layers are measured while moving a substrate or the illuminating means and the imaging means in the direction across a plurality of fluorescent layers applied to the substrate with predetermined intervals, and application volume for each fluorescent layer is measured from the obtained signals.

Preferably, in the display panel inspection method of the present invention, a roller may be used in the above movement.

Preferably, in the display panel inspection method of the present invention, there may be a moving speed measuring means for measuring the relative speed of the substrate to the imaging means.

Preferably, in the display panel inspection method of the present invention, the illuminating means irradiates ultraviolet rays of the wavelength of 260 nm or under on fluorescent layers, and the fluorescence photogenesis from the fluorescent layers is captured by the imaging means.

Preferably, in the display panel inspection method of the present invention, the signals obtained by the imaging means are corrected by the relative speed obtained by the moving speed measuring means, and the application volume for each fluorescent layer is measured by the corrected signals.

Preferably, in the display panel inspection method of the present invention, the moving speed measuring means calculates the speed from the interval of the fluorescent layers obtained by the imaging means.

Preferably, in the display panel inspection method of the present invention, fluorescent layers are liquid.

Preferably, in the display panel inspection method of the present invention, the imaging means mainly captures the light which is reflected at a substantially same angle as the angle of incidence of the incoming light out of the light irradiated from the illuminating means on the fluorescent layers and reflected thereby.

Preferably, in the display panel inspection method of the present invention, the illuminating means has a light diffusing means for diffusing the ejection light.

Preferably, in the display panel inspection method of the present invention, the illuminating means has a light polarizing direction selecting means for selecting the light of a desired polarized light direction among ejection light.

Preferably, in the display panel inspection method of the present invention, the shape of an ejection port of the illuminating means for ejecting the light is slit-shaped.

Preferably, in the display panel inspection method of the present invention, the width of the slit is 0.3 mm or over and 10 mm or under, and the length of the slit is 10 mm or over and 1000 mm or under.

Preferably, in the display panel inspection method of the present invention, the imaging means has a plurality of light receiving elements.

Preferably, in the display panel inspection method of the present invention, the imaging means further has the light receiving elements arrayed in a one-dimensional manner.

Preferably, in the display panel inspection method of the present invention, a signal processing means adds the signals of a plurality of light receiving elements of the imaging means and averages them, obtains a signal peak for each phosphor from the averaged signal waveform, obtains the signal peak waveform for each phosphor by linking the signal peaks, and measures the application volume of each fluorescent layer from the signal peak waveform.

Preferably, in the display panel inspection method of the present invention, the imaging means has a light polarizing direction selecting means for selecting the light of a desired polarized light direction from the reflected light.

Preferably, in the display panel inspection method of the present invention, the illuminating means irradiates ultraviolet rays of the wavelength of 360 nm or under, and the imaging means mainly captures ultraviolet rays of the wavelength of 360 nm or under.

Preferably, in the display panel inspection method of the present invention, inequalities 1 are satisfied, where R is the resolution of the imaging means, and $L_\alpha$ is the width of the grooves which are formed of partition walls with phosphor applied thereto.

$$3 \leq \frac{L_\alpha}{R} \leq 10$$

Preferably, in the display panel inspection method of the present invention, the signal processing means calculates the intensity of the inspection light incident on a substrate from the illuminating means based on the signals obtained by the imaging means, and corrects the illuminating means so that the intensity of the inspection light in the inspection of a next substrate becomes the preset target value with reference to the obtained intensity of the inspection light.

The display panel inspection method of the present invention is characterized in that the fluorescent layers are formed by application to a plurality of grooves formed of the partition walls, at least the reflected light at the angle of incidence θ out of the light incident on the surface of the fluorescent layers at the angle of incidence θ is captured, and the angle of incidence θ forms an angle at which the reflected light at the angle of reflection θ obtained by allowing the light to be incident on a groove bottom part without any phosphor applied thereto at the angle of incidence θ is blocked by the partition walls.

Preferably, in the display panel inspection method of the present invention, the angle of incidence θ satisfies the following inequalities 2, where H is the height of the partition walls forming the groove, $H_p$ is the surface height of phosphor, $L_\alpha$ is the width of the groove formed of the partition walls with phosphor applied thereto, and $L_\beta$ is the width of the groove formed of the partition walls without any phosphor applied thereto.

$$\tan^{-1}\frac{2(H-H_p)}{L_\alpha} < \theta \leq \tan^{-1}\frac{2H}{L_\beta}$$

A display panel inspection device of the present invention comprises an illuminating means and an imaging means, and is characterized in that the illuminating means and the imaging means are installed so as to irradiate the light and capture the image of the light at the angle of light incidence/reflection θ at which the reflected light from a groove bottom part without any phosphor applied thereto is blocked by the partition walls.

Preferably, in the display panel inspection device of the present invention, the angle of incidence θ satisfies the following inequalities 3, where H is the height of the partition walls forming the groove, $H_p$ is the surface height of phosphor, $L_\alpha$ is the width of the groove formed of the partition walls with phosphor applied thereto, and $L_\beta$ is the width of the groove formed of the partition walls without any phosphor applied thereto.

$$\tan^{-1}\frac{2(H-H_p)}{L_\alpha} < \theta \leq \tan^{-1}\frac{2H}{L_\beta}$$

Preferably, in the display panel inspection device of the present invention, the following inequalities 4 are satisfied, where F is the F number of the imaging means.

$$1.2 \leq F \leq 2.0$$

Preferably, in the display panel inspection device of the present invention, the received light intensity attenuating means is provided, and the following inequalities 5 are satisfied, where OD is the OD value of the received light intensity in the visible light area.

$$0.3 \leq OD \leq 2.0$$

The display panel inspection device of the present invention is characterized in that a mask having an aperture only in a part with phosphor to be inspected present therein is installed on an inspection surface of a substrate.

A display panel manufacturing method of the present invention is characterized in that an inspecting means for inspecting the application volume of fluorescent layers between an applying step and a drying step is provided, in the display panel manufacturing method comprising the applying step of applying phosphor on the substrate and the drying step of phosphor.

Preferably, in the display panel manufacturing method of the present invention, the following inequalities 6 are satisfied, where H is the height of the partition walls forming the groove, and $H_p$ is the surface height of phosphor.

$$0.6 < H_p/H < 0.9$$

Preferably, in the display panel manufacturing method of the present invention, a plurality of grooves have at least two kinds of groove width, and phosphor is applied successively from the groove of the widest interval between the partition walls in the display panel manufacturing method with the same kind of phosphor applied to the plurality of grooves having the same groove width.

Preferably, in the display panel manufacturing method of the present invention, an inspecting means for inspecting the application volume of the fluorescent layer is the inspection method according to aspects of the invention, and inspects a part in which the fluorescent layer emits the light at least when a substrate is built in by a panel.

Preferably, in the display panel manufacturing method of the present invention, a fluorescent layer repairing means is provided, and the fluorescent layer is repaired based on the result of the inspection of the inspecting means.

Preferably, in the display panel manufacturing method of the present invention, an inspecting means for inspecting the application volume of the fluorescent layer is the inspection method according to aspects of the invention, and when defects occur the applying step is stopped and troubles in the applying step are repaired.

Preferably, in the display panel manufacturing method of the present invention, an inspecting means for inspecting the application volume of the fluorescent layer is the inspection method according to aspects of the invention, the applying step is a nozzle applying method, and a nozzle is changed when defects occur.

Preferably, in the display panel manufacturing method of the present invention, an inspecting means for inspecting the application volume of the fluorescent layer is the inspection method according to aspects of the invention, the applying step is a nozzle applying method, and when defects occur the clogged nozzle is identified, and clogged thing of the nozzle is removed by the vibration.

A display panel manufacturing device of the present invention inspects a pattern formed on the substrate, and is characterized in that this manufacturing device comprises a light irradiating means for irradiating the light on the pattern, an imaging means for receiving the light from the pattern and outputting image signals, a moving means for relatively moving the substrate to the imaging means, a moving speed measuring means for measuring the substrate to the imaging means, and a signal processing means for correcting the image signals by the obtained relative speed and comparing the corrected image signals with a predetermined reference value, and determining acceptance/rejection of the pattern based on the difference/coincidence from/with the reference value.

A display panel manufacturing method of the present invention is characterized in that an inspecting steps for inspecting the application volume of liquid phosphor between an applying step and a drying step is provided, in the display panel manufacturing method comprising the applying step of applying a plurality of sets of liquid phosphor with predetermined intervals on the substrate and the drying step of drying liquid phosphor to form fluorescent layers.

REFERENCE NUMERALS

Figure 1:
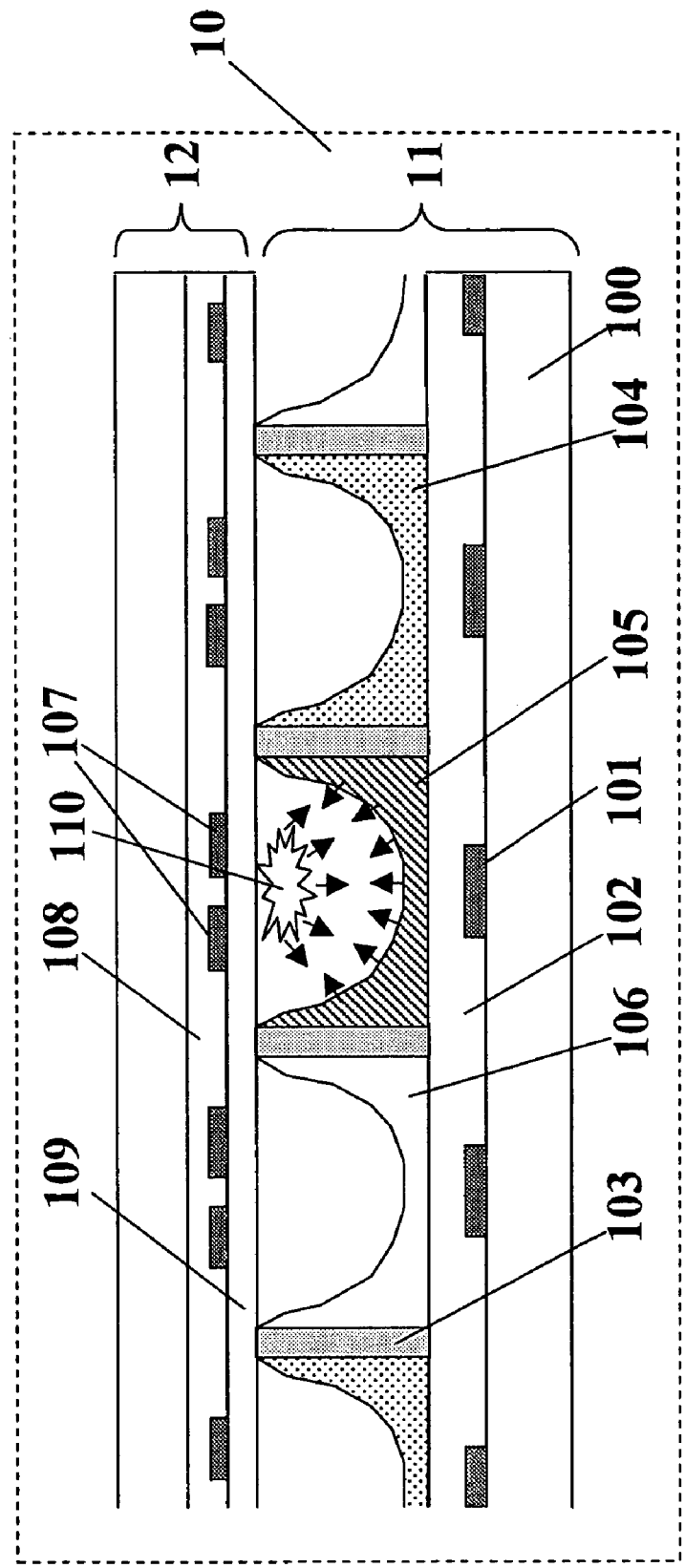
FIG. 1 is a schematic cross-sectional view to simply show the configuration of a back plate of a PDP.

10: PDP
11: back plate of PDP
12: front plate of PDP
100: glass substrate
101: address electrode
102: dielectric layer
103: partition wall
104: red fluorescent layer
105: green fluorescent layer
106: blue fluorescent layer
107: display electrode
108: dielectric layer
109: protective layer
110: plasma
111: transverse rib 115: groove of groove width L formed by partition walls
116: groove of groove width L1 formed by partition walls
117: groove of groove width L formed by partition walls
118: groove of groove width L formed by partition walls
119: groove of groove width L formed of partition walls and transverse ribs
120: cell
210: step of cleaning and drying a glass substrate
220: step of forming a straight pattern electrode
230: step of forming a dielectric film
240: step of forming partition walls
250: step of forming a fluorescent layer between partition walls
251: step of applying liquid phosphor between partition walls
252: phosphor inspection step (I)
253: liquid phosphor drying step
254: phosphor inspection step (II)
260: step 260 of repairing defect portion of phosphor
261: defect repairing step (I)
622: defect repairing step (II)
300: substrate having grooves
310: substrate having grooves of three kinds of groove width
320: substrate having grooves with transverse ribs
330: substrate having defect in liquid phosphor
331: substrate having defect in fluorescent layer
600, 602, 1500, 1502, 1600, 1602, 2100, 2102: liquid phosphor normally applied to each groove
601, 1501, 1601, 2101: liquid phosphor having portion not applied to grooves
603, 1503, 1603, 2103: liquid phosphor which should have been applied to grooves, but not applied thereto
610, 612, 1510, 1512, 1610, 1612, 2110, 2112: reflected light brightness peak from the surface of liquid phosphor
611, 1511, 1611, 2111: reflected light brightness peak from the surface of liquid phosphor having portion not applied to grooves
613, 1513, 1613, 2113: reflected light brightness peak from non-applied liquid phosphor
620, 720, 1520, 1620, 2120: brightness signal waveform
630, 632: extracted value of reflected light brightness peak from the surface of liquid phosphor
631: extracted value of reflected light brightness peak from the surface of liquid phosphor having portion not applied to grooves
633: extracted value of reflected light brightness peak from non-applied liquid phosphor
640, 740: brightness peak waveform
650, 750, 1630, 1631: threshold
660: graph showing brightness change at the position of the dotted line s
670: graph showing brightness peak extracted from brightness change at the position of the dotted line s
700, 702: fluorescent layer normally formed in each groove
701: fluorescent layer formed in the amount less than the standard value
703: fluorescent layer which should have been formed in grooves, but not formed
710, 712: brightness peak of fluorescent photogenesis of fluorescent layer
711: brightness peak of fluorescent photogenesis of fluorescent layer formed in the amount less than the standard value
713: brightness peak of fluorescent photogenesis of non-formed fluorescent layer
730, 732: extracted value of brightness peak of fluorescent photogenesis of fluorescent layer
731: extracted value of brightness peak of fluorescent photogenesis of fluorescent layer formed in the amount less than the standard value
733: extracted value of brightness peak of fluorescent photogenesis of non-formed fluorescent layer
760: graph indicating brightness change at the position of the dotted line t
770: graph indicating brightness peak extracted from brightness change at the position of the dotted line t
900: groove section without any application of phosphor
901: part capable of reflecting the reflected light within angular aperture of groove
1000: section of liquid phosphor of concave surface
1001: part capable of reflecting the reflected light within angular aperture of liquid phosphor of concave surface
1100: section of liquid phosphor of flat surface
1101: part capable of reflecting the reflected light within angular aperture of liquid phosphor of flat surface
1200: section of liquid phosphor of convex surface
1201: part capable of reflecting the reflected light within angular aperture of liquid phosphor of convex surface
1300, 1401, 1402, 1403: parallel light
1301, 1302, 1303: diffused light
1301', 1302', 1303', 1401', 1402', 1403': reflected light
1310: light diffusing means
1320: imaging means
1330, 1430: completely flat surface with respect to substrate surface
1331, 1431: area including a part of completely flat surface and non-flat surface with respect to substrate surface
1420: small imaging angular aperture
1421: large imaging angular aperture
1550: graph indicating brightness change at the position of the dotted line u
1610'; 1612': reflected light brightness peak from liquid phosphor surface after optimizing the angle of incidence/reflection of light
1611': reflected light brightness peak from the surface of liquid phosphor having non-applied portion to grooves after optimizing the angle of incidence/reflection of light
1613': reflected light brightness peak from non-applied liquid phosphor after optimizing the angle of incidence/reflection of light
1614': reflected light brightness peak from the surface of liquid phosphor applied more in amount than appropriate value after optimizing the angle of incidence/reflection of light
1620': brightness signal waveform after optimizing the angle of incidence/reflection of light
1650: graph indicating brightness change at the position of the dotted line v
1650': graph indicating brightness change at the position of the dotted line v after optimizing the angle of incidence/reflection of light
1700: state of incidence/reflection of the light at angle θ' by groove bottom part
1800: state of incidence/reflection of the light at angle θ' by liquid phosphor surface
1900: state of incidence/reflection of the light at angle θ by groove bottom part
2000: state of incidence/reflection of the light at angle θ by liquid phosphor surface
2130: mask formed of material of low light reflectance
2150: graph indicating brightness change at the position of the dotted line w 2200: liquid phosphor applied different in amount for each cell
2201: liquid phosphor of flat surface applied to cell
2202, 2204: liquid phosphor of concave surface applied to cell
2203: liquid phosphor of convex surface applied to cell
2250: graph indicating brightness change at the positions of the dotted lines x and x'
2260: graph indicating brightness change obtained by averaging signals for width y between the dotted lines x and x'
2210: reflected light brightness peak from the surface of liquid phosphor of concave surface
2210': reflected light brightness peak from the surface of liquid phosphor of flat surface
2211: reflected light brightness peak from the surface of liquid phosphor obtained by averaging signals
2220: brightness signal waveform obtained from liquid phosphor of concave surface shape
2220': brightness signal waveform obtained from liquid phosphor of flat surface shape
2221: brightness signal waveform obtained by averaging brightness signal by predetermined width
2300: brightness signal waveform when the substrate carrying speed is changed
2301: brightness peak interval
2302: apparent brightness peak interval
2303: brightness peak interval when the substrate carrying speed is changed
2304: period in which the substrate carrying speed is changed
2310: defect point
2320: substrate carrying speed waveform
2350: graph indicating brightness signal waveform when the substrate carrying speed is changed
2360: graph indicating substrate carrying speed waveform
2400: fluorescent layer with the amount of phosphor less than the standard value
2401: fluorescent layer with the standard amount of phosphor
2402: fluorescent layer with the amount of phosphor more than the standard value
2410: hem of fluorescent layer
2420: incoming light
2430, 2431, 2432, 2460: scattering light
2440: imaging means
2450: dielectric layer
2521: light of wavelength of 260 nm or under
2540, 2541, 2542: fluorescent photogenesis
2701: incoming light
2702: reflected light
2703: fluorescent photogenesis
2710: illuminating means
2711: light source part
2712: light transmission part
2713: light ejection port
2714: light diffusing means
2715, 2723: light polarizing direction selecting means
2720: imaging means
2721: light receiving part
2722: light converging part
2724: received light intensity attenuating means
2725: imaging wavelength selecting means
2731: signal processing means
2732: signal transmitting means
2741: moving means
2742: substrate carrying means
2743: angle adjusting mechanism
2751: substrate advancement sensing means
2752: substrate moving speed measuring means
2800: target light requirement setting stage
2810: inspection starting stage
2820: waiting stage
2830: image capturing stage
2840: signal processing stage
2850: inspection result outputting stage
2860: inspection finishing stage
2871: light reception acquiring stage
2872: illuminating means control calculating stage
2873: light quantity adjusting stage
2901, 2902, 3001, 3002: (part of) defect
3003: repaired defect
2910, 3010: nozzle for repairing defect
2920, 3020: liquid phosphor
E, F, G, I, J, K, M, N: partition wall
H: height of partition wall
$H_p$: surface height of phosphor
L, L, L, L: predetermined groove width
Lp: groove width for three colors of RGB
P0: brightness of reflected light obtained without any application of phosphor
P1: brightness of reflected light obtained when application volume of liquid phosphor is V1
P2: brightness of reflected light obtained when application volume of liquid phosphor is V2
P3: brightness of reflected light obtained when application volume of liquid phosphor is V3
Q, R: curve indicating the relationship between surface shape (application volume) of liquid phosphor and the intensity of reflected light
U: curve indicating the relationship between amount of phosphor and the intensity of reflected light
V0, V1, V2, V3: application volume of liquid phosphor (V0=0<V1<V2<V3)
X: curve indicating the relationship between amount of phosphor and the intensity of fluorescent photogenesis
a, b, c, d, e, f, g, h, i, j, k, l: groove of groove width L formed of partition walls
a', d', g', j': groove of groove width L formed of partition walls
b', e', h', k': groove of groove width L formed of partition walls
c', f', i', l': groove of groove width L formed of partition walls
m, n, o, p: constant
s, t, u, v, w, x, x': position of obtaining brightness signal waveform from substrate to be inspected
y: integrated width of brightness signal

BEST MODE FOR CARRYING OUT THE INVENTION

The embodiments of the present invention will be described with a back plate of a PDP as an example with reference to the drawings.

Firstly, the basic configuration of the PDP will be briefly described using FIG. 1. FIG. 1 is a schematic cross-sectional view simply indicating the configuration of the back plate of the PDP. A PDP 10 comprises a back plate of the PDP 11 on a back glass substrate 100 in which a partition wall 103 is disposed on a dielectric layer 102 with an address electrode 101 disposed thereon, and RGB fluorescent layers 104, 105, 106 are coated therebetween, and a front glass substrate 12 with a dielectric layer 108 with display electrodes 107 (displayed in a rotational manner by 90°) and a protective layer 109 interposed therein.

Here, the principle of emission of a plasma display will be described below. Plasma 110 is generated by sealing mixture gas which consists of neon or xenon in a space between the display electrode 107 and the address electrode 101, and applying the voltage thereto, a phosphor at the selected position emits light thereby, and a desired color is displayed by the combination of light emission of each phosphor.

Figure 2:
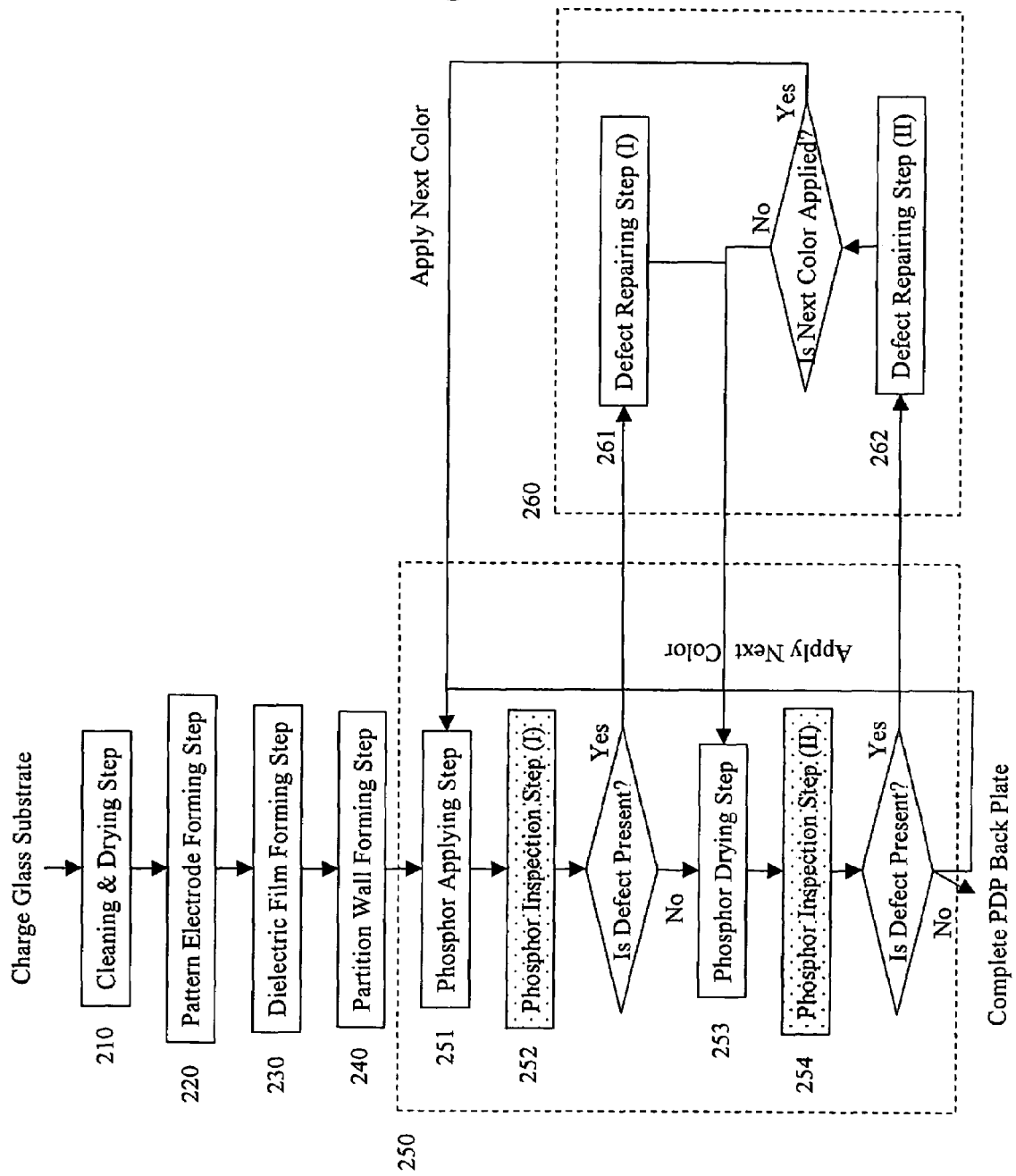
FIG. 2 is a flowchart showing an example of an embodiment.

Next, a manufacturing method of a flat display panel will be described with reference to FIG. 2 with a back plate of the PDP as an example. FIG. 2 is a flowchart simply showing a manufacturing step of the back plate of the PDP. The manufacturing method of the back plate of the PDP comprises a step 210 of cleaning and drying a glass substrate forming a base of the back plate of the PDP, a step 220 of forming a straight pattern electrode of a conductive material, a step 230 of forming a dielectric film on the glass substrate, a step 240 of forming partition walls, a step 250 of forming a fluorescent layer between the respective partition walls, and a step 260 of repairing a defective portion of a phosphor. The step 250 of forming the fluorescent layer between the partition walls will be described below in detail. This step 250 comprises a step 251 of applying liquid phosphor between the partition walls, a first step 252 of inspecting a forming state of a phosphor (hereinafter, referred to as phosphor inspection step (I)), a step 253 of drying liquid phosphor to form the fluorescent layer, and a second step 254 of inspecting a phosphor forming state (hereinafter, referred to as phosphor inspection step (II)). The step 260 of repairing the defective portion of the phosphor will be described below in detail. This step comprises a step 261 of repairing a defect discovered in the phosphor inspection step (I) (hereinafter, referred to as a defect repairing step (I)), and a step 262 of repairing a defect discovered in the phosphor inspection step (II) (hereinafter, referred to as a defect repairing step (II)).

In addition, in order to realize desired color display in the PDP by using three kinds of RGB color development, it is necessary to form the fluorescent layer of three colors of RGB as shown in FIG. 1, and the step 250 of forming the fluorescent layer between the partition walls is repeated three times.

In particular, the present invention relates to the phosphor inspection step (I) 252 and the phosphor inspection step (II) 254. The present invention is characterized in that the optimum optical condition for the optical inspection of the phosphor is determined according to the structural characteristic of the substrate which is an object for inspection, the determined condition is reflected on an inspection apparatus to carry out the inspection with excellent accuracy, causes of abnormalities in the step are estimated by information on defects if any defective substrate is generated, the step is immediately corrected to prevent any defects in the fluorescent layer, and the yield is ensured by rapidly repairing the defective substrate.

Figure 3:
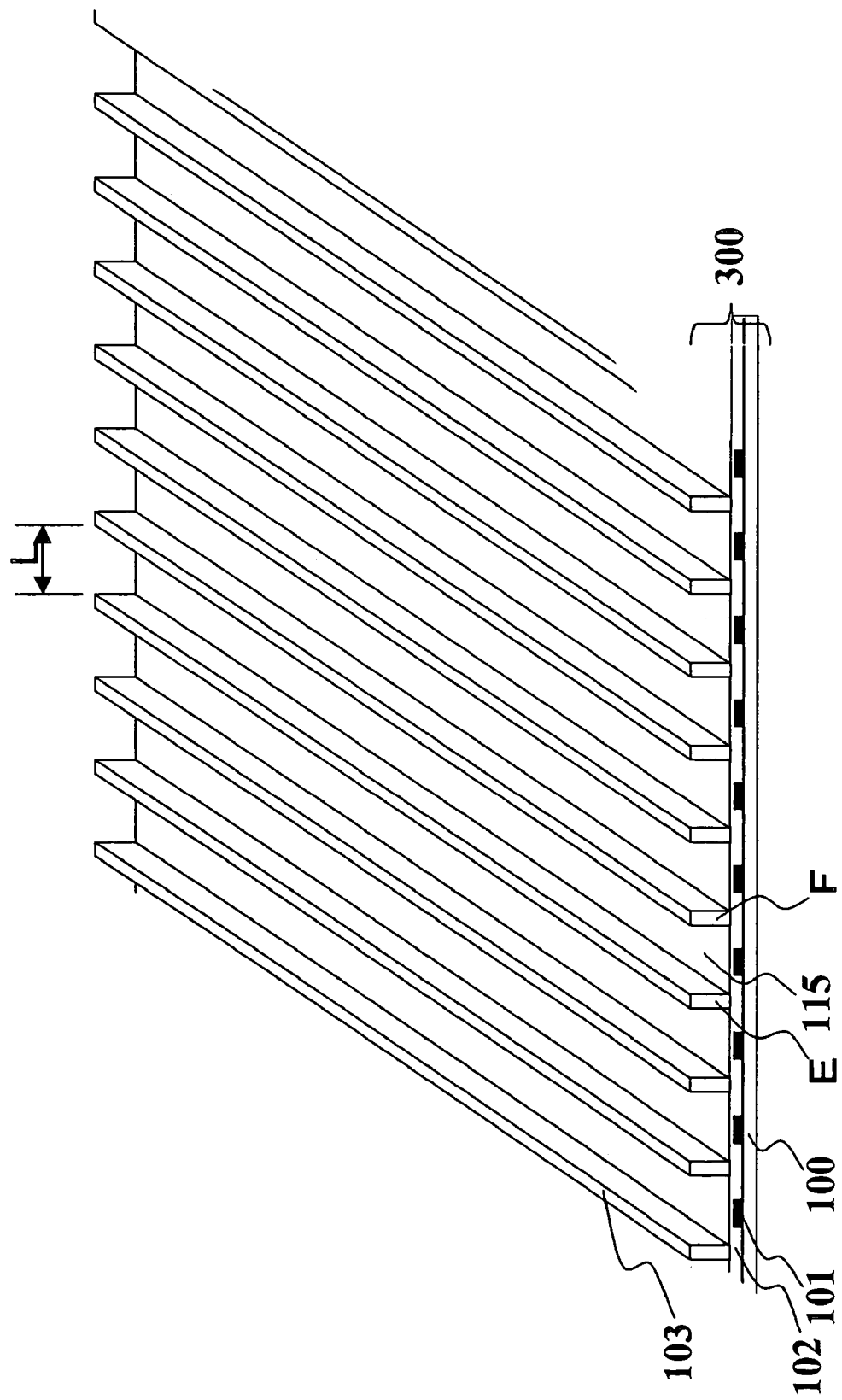
FIG. 3 is a schematic illustration of a substrate having grooves.

Next, the substrate with the fluorescent layer disposed thereon will be described with reference to FIGS. 3, 4 and 5. FIG. 3 is a schematic illustration of the substrate having grooves, FIG. 4 is a schematic illustration of the substrate having grooves of three kinds of groove width, and FIG. 5 is a schematic illustration of the substrate having grooves sectioned for predetermined space in the longitudinal direction by the partition walls, respectively.

In FIG. 3, a substrate 300 comprises a glass substrate 100, a plurality of straight pattern electrodes 101, a dielectric film 102, and a plurality of partition walls 103. On the substrate 300, a space between the partition walls held by, for example, a partition wall E and a partition wall F out of the plurality of partition walls 103 is defined as a groove 115. As a matter of course, a plurality of grooves of the same width L are formed on the substrate 300.

Figure 4:
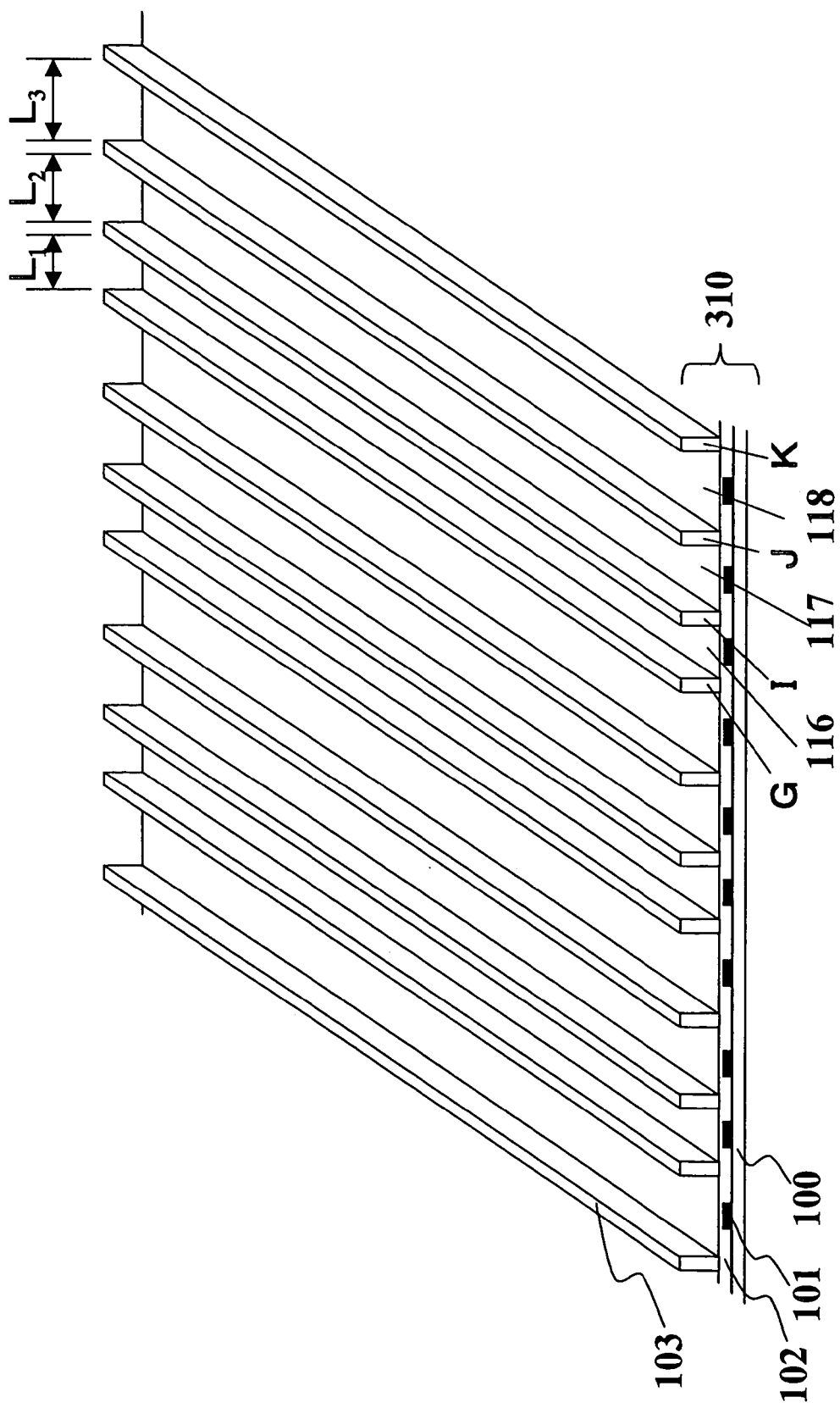
FIG. 4 is a schematic illustration of a substrate having grooves of three kinds of groove width.

In FIG. 4, the substrate 310 comprises a glass substrate 100, a plurality of straight pattern electrodes 101, a dielectric film 102, and a plurality of partition walls 103. On the substrate 310, a space between the partition walls held by, for example, a partition wall G and a partition wall I out of the plurality of partition walls 103 is defined as a groove 116, a space between partition walls held by the partition wall I and a partition wall J out of the plurality of partition walls 103 is defined as a groove 117, and a space between partition walls held by the partition wall J and a partition wall K out of the plurality of partition walls 103 is defined as a groove 118, respectively. This means that three kinds of the grooves 116, 117 and 118 are constituted orderly on the substrate 400 so that the groove width satisfies the inequalities of $L1<L2<L3$. The kind of the grooves is preferably at least two, but not limited to three as shown in FIG. 4.

Figure 5:
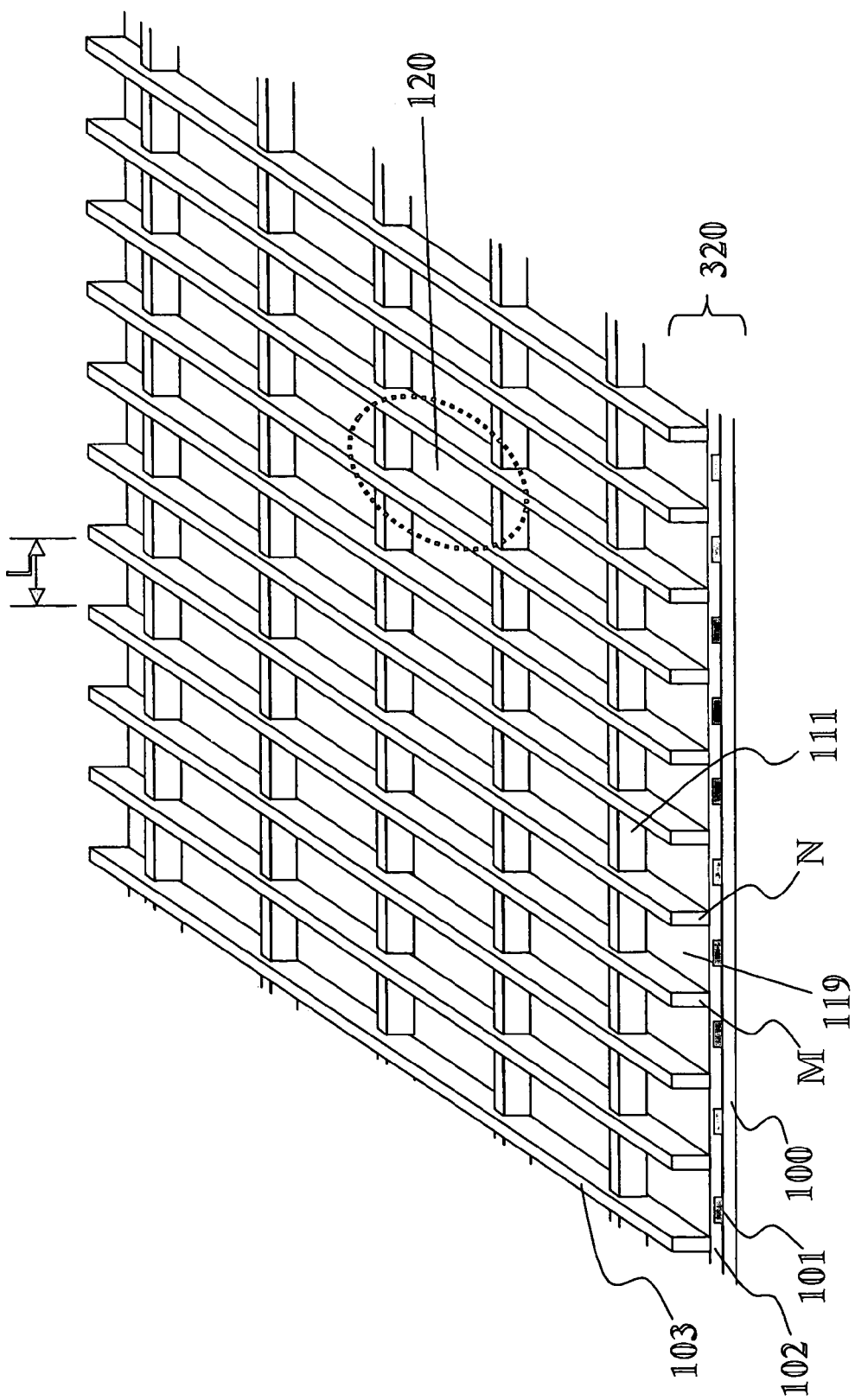
FIG. 5 is a schematic illustration of a substrate having grooves with transverse ribs.

In FIG. 5, a substrate 320 comprises a glass substrate 100, a plurality of straight pattern electrodes 101, a dielectric film 102, a plurality of partition walls 103, and another partition wall 111 (hereinafter, referred to as "transverse rib") formed in the direction orthogonal to the partition wall 103. On the substrate 320, a part held by, for example, a partition wall M and a partition wall N out of the plurality of partition walls 103 is defined as a groove 119 having transverse rib, and a part section by the partition wall 103 and the transverse rib 111 is defined as a cell 120. Further, in FIG. 5, the groove width of the plurality of grooves 119 having transverse ribs is constant, but a plurality of kinds of groove width as shown in FIG. 4 may be acceptable.

Figure 6:
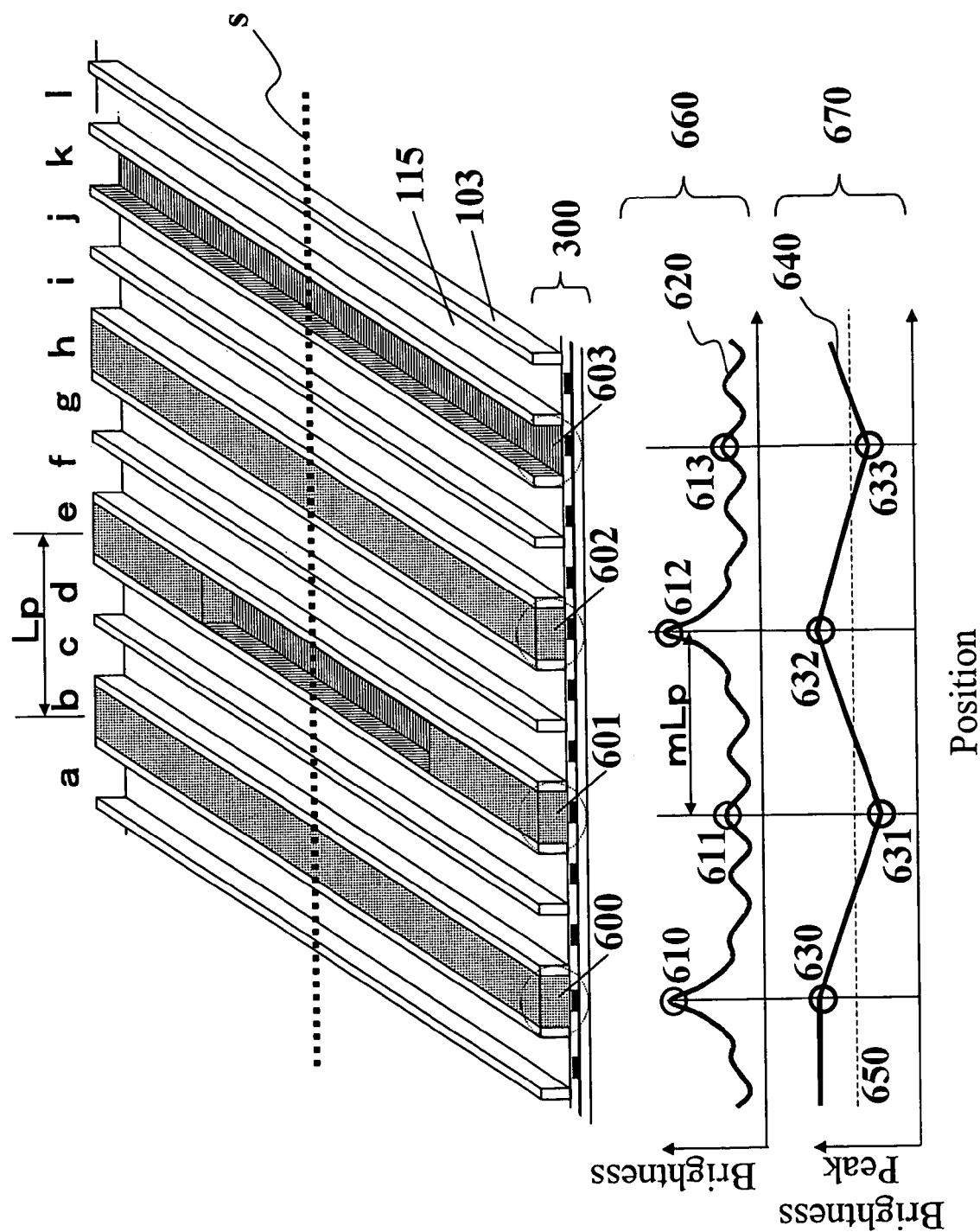
FIG. 6 is a schematic illustration of liquid phosphor applied to a substrate having grooves so that a surface shape is flat, and brightness signal waveform obtained by an inspection method of the present invention.

Next, the substrate with liquid phosphor is applied thereto by performing the step 251 of applying liquid phosphor between partition walls on the substrate 300 in which a fluorescent layer shown in FIG. 3 is formed will be described as an example with reference to FIG. 6. FIG. 6 is a schematic illustration indicating the liquid phosphor applied to the groove and brightness signal waveform obtained by the phosphor inspection step (I) of the present invention.

As described above, in order to realize desired color display by using three kinds of RGB color development in the PDP, it is necessary to form RGB fluorescent layers in a predetermined repeated order (for example,: BRGBRG:) as shown in FIG. 1. Thus, if attention is made to a certain color of RGB, the certain color must be applied orderly across two grooves as shown by liquid phosphor 600, 601, 602 and 603 applied to the grooves b, e, h and k in FIG. 6. In liquid phosphor applied to the desired grooves, solvent component is removed by performing the drying step 253, and the fluorescent layer is formed on the groove.

In addition, in FIG. 6, the fluorescent layers have not been formed on the grooves a, c, d, f, g, i, j and l. However, the fluorescent layers of another or two other colors have possibly already been formed due to the schedule of the step.

Figure 7:
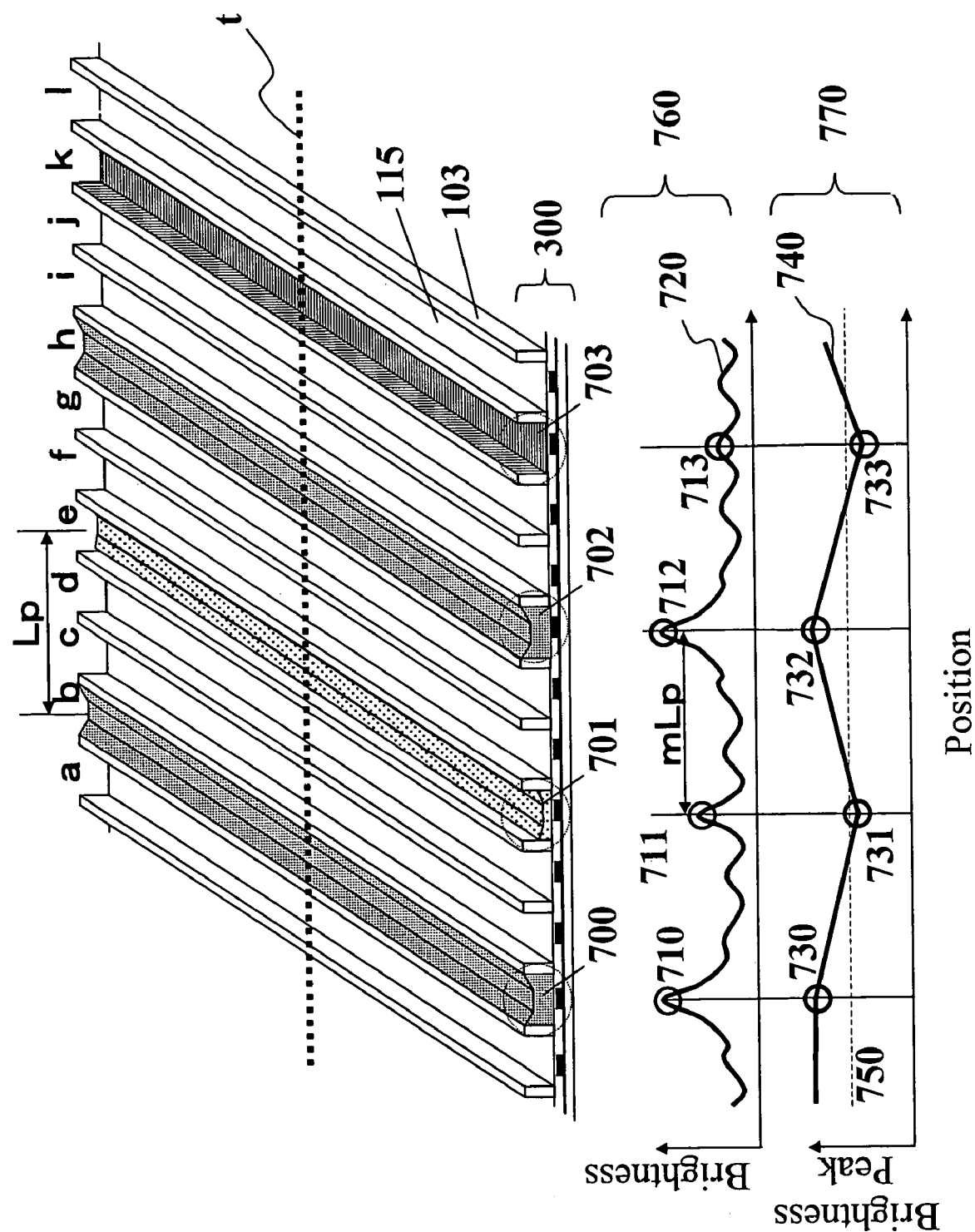
FIG. 7 is a schematic illustration of a fluorescent layer formed on a substrate having grooves, and brightness signal waveform obtained by an inspection direction of the present invention.

As a still another example, the substrate with the fluorescent layer of a certain color formed thereon by performing the step 250 of forming the fluorescent layer between the partition walls on the substrate 300 with the fluorescent layer shown in FIG. 3 formed thereon will be described with reference to FIG. 7. FIG. 7 is a schematic illustration indicating the fluorescent layer of a certain color formed on the groove and the brightness signal waveform obtained by the phosphor inspection step (II) of the present invention. As described above, the fluorescent layers 700, 701, 702 and 703 must be formed orderly on the grooves b, e, h and k across two grooves. In FIG. 7, due to an abnormality in the step, the amount of phosphor on the fluorescent layer 701 is smaller than the standard value, and any fluorescent layer is not formed in the groove k in which the fluorescent layer should be present. By performing the step 250 of forming the fluorescent layer for two other colors, the RGB fluorescent layers will be formed in a predetermined repeated order (for example,: BRGBRG:)

One of especially important factors for determining luminous brightness in PDP includes the amount of phosphor in the fluorescent layer. There is a tendency in that the brightness is lower if the amount of phosphor is small while the brightness is higher if the amount of phosphor is large, and if no phosphor is applied, no light emission occurs as a matter of course. In addition, if grooves of the large, small and no amount of phosphor are present in a mixed manner in one substrate, these grooves cause irregularities in luminous brightness of the PDP, naturally resulting in defective products. The worst cause of the phenomenon that the amount of phosphor of the fluorescent layer is not consistent is irregularities in liquid phosphor application when liquid phosphor is applied to grooves.

Generally known methods of applying liquid phosphor to desired grooves include screen printing, photo-lithographic processing, and nozzle application. If any trouble occurs in application of liquid phosphor by these methods, a part without any application of liquid phosphor is generated as shown as 601 in FIG. 6, or a groove to which liquid phosphor is not completely applied as in 603 is generated. If any substrate having troubles in such a state of application of liquid phosphor is subjected to the step 253 of forming the fluorescent layer by drying liquid phosphor, a defective substrate having a fluorescent layer of different amount of phosphor on one substrate is manufactured.

In addition, causes of generation of irregularities in application by the above liquid phosphor applying method includes clogging of a screen and defective adjustment of a phosphor applicator in the screen printing, defective adjustment of the phosphor applicator and adhesion of foreign matters to a photo mask in the photo-lithographic processing, and clogging of nozzle holes and non-uniformity in application pressure caused by abnormalities of a pressurizing device, and if troubles in application attributable thereto occur once, they will cause continuous defects in the total substrates.

An inspection method of a display panel of the present invention improves the yield of products by rapidly detecting continuous defects with high accuracy in order to prevent continuous shipment of the above defective substrates to subsequent steps in the phosphor inspection step (I) 252 and the phosphor inspection step (II) 254, estimating the causes of abnormalities in the steps from information on defects, correcting the step immediately to prevent any defects of irregularities in brightness generated in the fluorescent layer, and rapidly repairing any defective substrates.

In order to inspect the phosphor forming state, the above conventional technology can be used. This means that the phosphor forming state is inspected by the change in the obtained imaging brightness by allowing the light to be incident on the phosphor at a predetermined angle of incidence, and receiving the reflected light from the phosphor at a predetermined angle of reflection. However, if the object for inspection such as the back plate of the PDP has a complicated structural characteristic, and subjected to a large number of manufacturing steps, the manufacturing condition of the object is changed and the pattern shape forming the surface is changed unless adjusting the optical conditions such as the angle of incidence, the angle of reflection, the wavelength, the intensity, the scattering and the polarizing direction of the inspection light considering the structural characteristic of the object for inspection, and problems occur in that the inspection accuracy is considerably degraded, or the inspection cannot be carried out if the structural characteristic is different by the stage of the manufacturing step even when the products are same.

Description will be made below on the detailed problems of the conventional technology and the solution of problems in the inspection method of the present invention while comparing them with each other.

Firstly, description will be made on a case of carrying out the inspection in the phosphor inspection step (I) 254. At the time of the phosphor inspection step (I) 254, phosphor which is an object of inspection is applied as a liquid to a groove comprising partition walls on the substrate. Here, reflection of the reflected light at the angle of incidence of the incoming light is defined as the regular reflection, the reflected light which is regularly reflected is defined as the regularly reflected light, and the light reflected in the angular aperture when a predetermined angular aperture for capturing the light captures at least the regularly reflected light is defined as the reflected light in the angular aperture, respectively, and they are used below.

Figure 8:
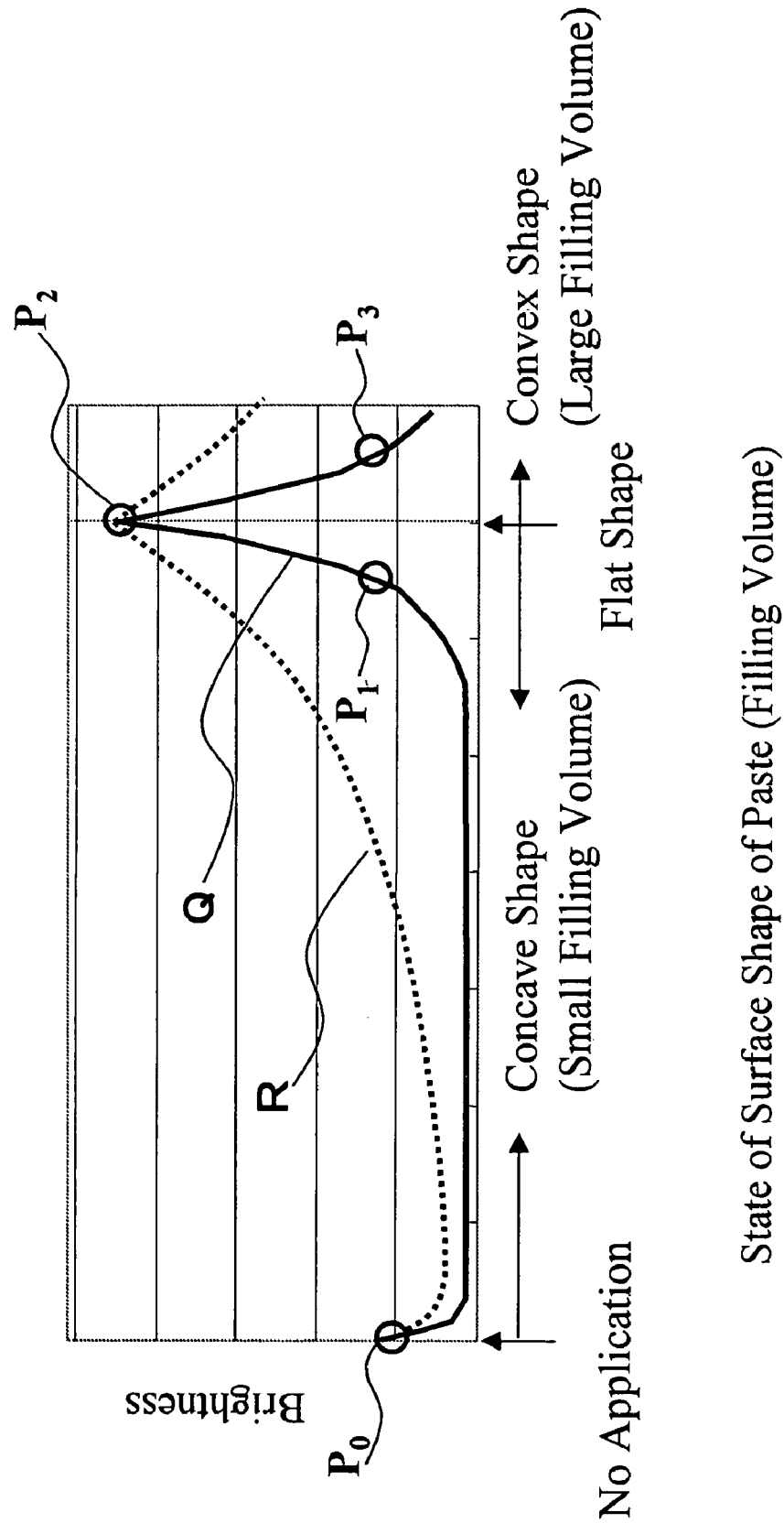
FIG. 8 is a schematic illustration indicating the relationship between the surface shape (application volume) of liquid phosphor and the intensity of the reflected light.

Here, the principle and problems of the inspection of the application state of liquid phosphor applied to the substrate by the conventional technology, in particular, the optical inspection technology for capturing the regularly reflected light are successively described with reference to FIGS. 6, 8, 9, 10, 11 and 12. FIG. 8 is a schematic illustration indicating the relationship between the surface shape (application volume) of liquid phosphor and the intensity of the reflected light (hereinafter, referred to as "surface shape—brightness correlation"). FIGS. 9, 10, 11 and 12 are schematic illustrations indicating the relationship between the liquid phosphor application volume and the surface shape after application thereof.

Firstly, the relationship between the application state of liquid phosphor and the obtained brightness of the reflected light will be successively described with reference to FIGS. 8, 9, 10, 11 and 12.

For easy understanding, a predetermined application volume V2 is defined as a reference. The surface shape of liquid phosphor in this case is flat (parallel to) with respect to the substrate surface as shown by the liquid phosphor 1100 in FIG. 11. With the application volume V1 (<V2) which is smaller than this reference, the surface shape of liquid phosphor is concave with respect to the substrate surface as shown by the liquid phosphor 1000 in FIG. 10. On the other hand, with the application volume V3 (>V2) which is larger than the reference, the surface shape of liquid phosphor is convex with respect to the substrate surface as shown by the liquid phosphor 1200 in FIG. 12.

Figure 9:
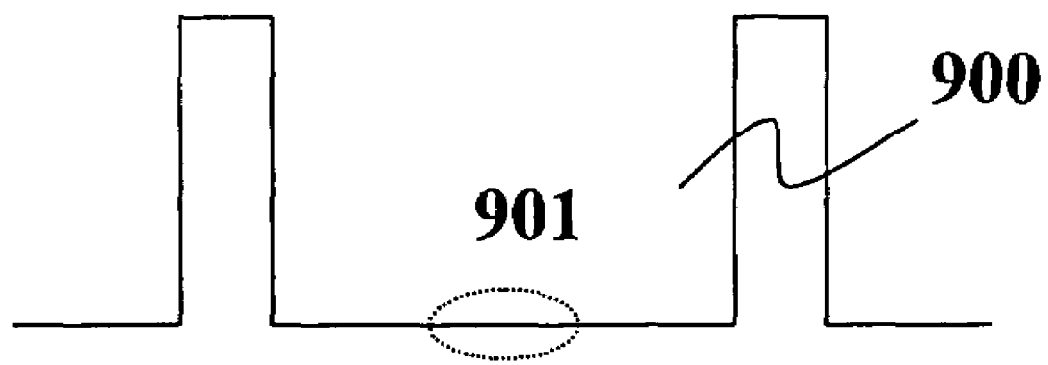
FIG. 9 is a schematic illustration the surface shape of the groove when any liquid phosphor is not applied.

In addition, with the application volume V0=0 (<V2) when non-application occurs in which any liquid phosphor is not applied completely, no liquid phosphor is present in the groove as shown by 900 in FIG. 9, and the surface shape is of concave shape constituted by the partition walls and the dielectric layer.

As described above, when the reflected light reflected by the surface of liquid phosphor is captured, the surface is flat in the reference liquid phosphor 1100, and the regularly reflected light from every area 1101 of the liquid surface can be captured, and the obtained brightness signal will be at a maximum.

Figure 10:
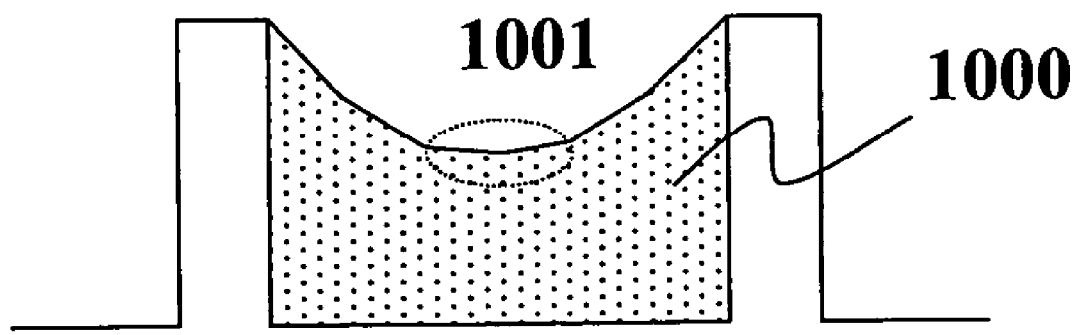
FIG. 10 is a schematic illustration of the surface shape after application of liquid phosphor when the application volume thereof is V1.
Figure 11:
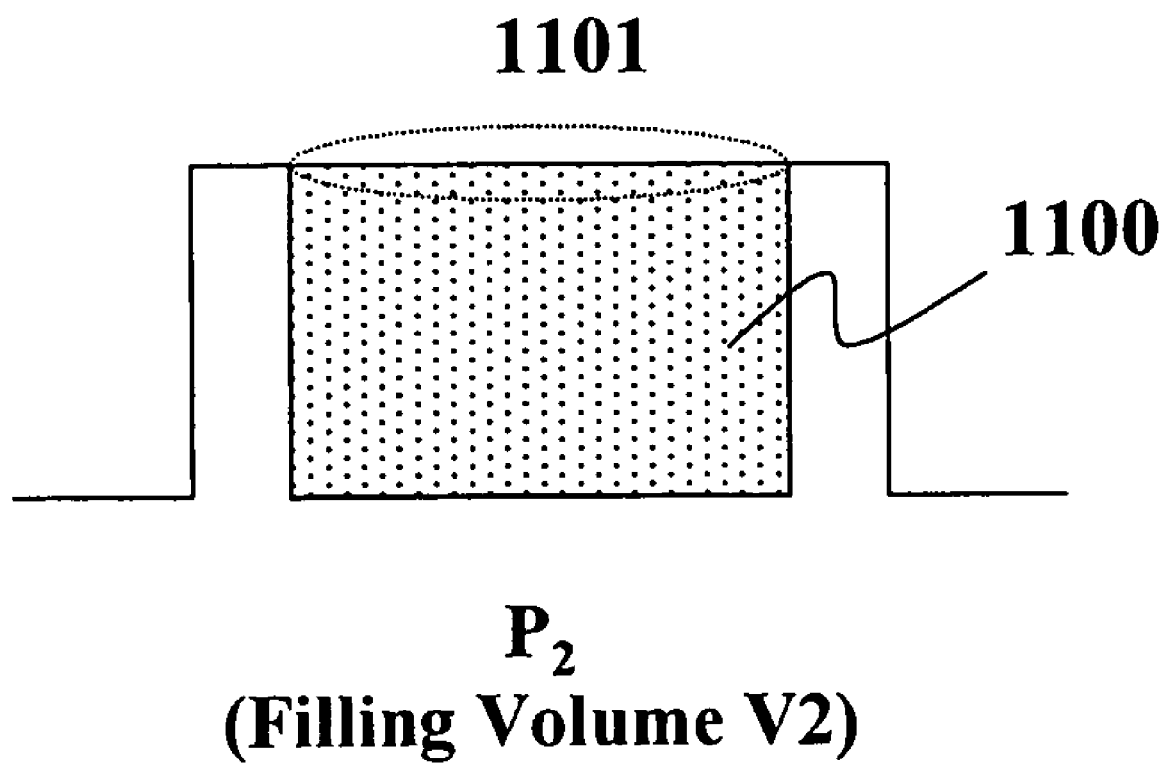
FIG. 11 is a schematic illustration of the surface shape after application of liquid phosphor when the application volume thereof is V2.

On the other hand, on the liquid phosphor 1000, a part capable of reflecting the reflected light in the angular aperture becomes an area 1001 shown in FIG. 10 since the surface is concave, and the obtained brightness signal becomes smaller than that by the liquid phosphor surface 1100. In addition, this effect becomes more remarkable as the application volume V becomes smaller, i.e., as the surface shape of liquid phosphor is considerably more concave than the flat shape.

Figure 12:
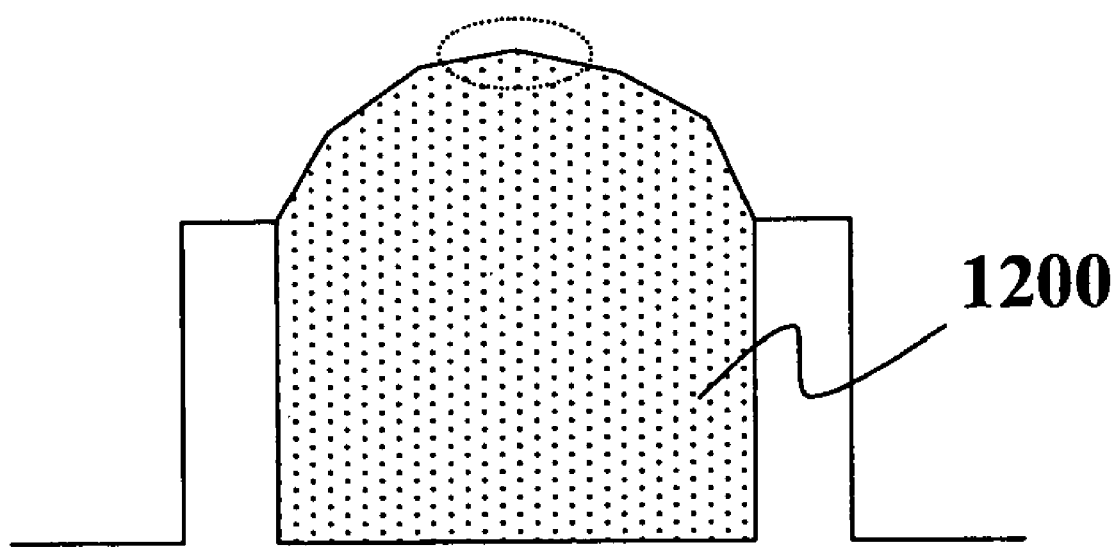
FIG. 12 is a schematic illustration of the surface shape after application of liquid phosphor when the application volume thereof is V3.

Further, in the liquid phosphor 1200, the surface shape is convex, the part capable of reflecting the reflected light in the angular aperture becomes an area 1201 shown in FIG. 12, and the obtained brightness signal becomes smaller than that of the liquid phosphor 1100. In addition, this effect becomes more remarkable as the application volume V becomes larger, i.e., as the surface shape of liquid phosphor is considerably more convex than the flat shape.

In the non-application state 900, the reflecting surface is flat, and regular reflection easily occurs. However, since a bottom part of a reflecting surface is lower than a part with liquid phosphor applied thereto, the reflected light in the angular aperture is easily blocked by the partition walls, the part capable of reflecting the reflected light in the angular aperture forms an area 901 shown in FIG. 9, and the obtained brightness signal is smaller than that of the liquid phosphor 1100.

The curve Q in FIG. 8 is a graph indicating the relationship between the liquid phosphor application volume, the liquid phosphor surface shape, and the obtained brightness with the brightness in Y-axis and with the liquid phosphor application volume or the liquid phosphor surface shape in X-axis. This means that the brightness becomes maximum when the surface of liquid phosphor is flat, and the obtained brightness becomes smaller when the surface shape is convex or concave or non-application of liquid phosphor. In the inspection of the application state of liquid phosphor by applying the conventional technology using an optical system capturing the regularly reflected light, the liquid phosphor application volume is measured by using the relationship between the liquid phosphor application volume, the liquid phosphor surface shape and the intensity of the obtained brightness, and determining non-defective or defective products.

A problem with the conventional technology includes that the correlation between the surface shape and the brightness is steeply changed in the vicinity of a flat surface shape as indicated by the curve Q in FIG. 8, and the brightness is changed less with other surface shapes. This means that the conventional technology has the inspection sensitivity only in a narrow range of the surface shape (application volume) around a part of flat surface shape of liquid phosphor. In other words, in the inspection utilizing the relationship of the curve Q, determination is only available for whether or not the surface shape of liquid phosphor is flat. In order to measure the surface shape of liquid phosphor, i.e., the application volume with high accuracy in a wide range of surface shapes (application volume) from non-application to flat surface shape, the correlation between the surface shape and the brightness must be substantially proportional as a curve R in FIG. 8.

In the conventional technology, the reason why the correlation between the surface shape and the brightness is expressed like the curve Q is that an imaging means is strongly apt to capture only the reflected light from the surface completely flat with respect to the substrate surface in the conventional technology. To solve the problem, the correlation between the surface shape and the brightness shown by the curve R can be obtained if constituting an optical system for capturing the reflected light from an area including the surface completely flat with respect to the substrate surface and the one part of no-flat surface. Thus, in the inspection method of the present invention, it is devised that the diffusivity of the inspection light is increased, and the image capture angular aperture of the imaging means is extended. These devices will be described with reference to FIGS. 13 and 14.

Figure 13:
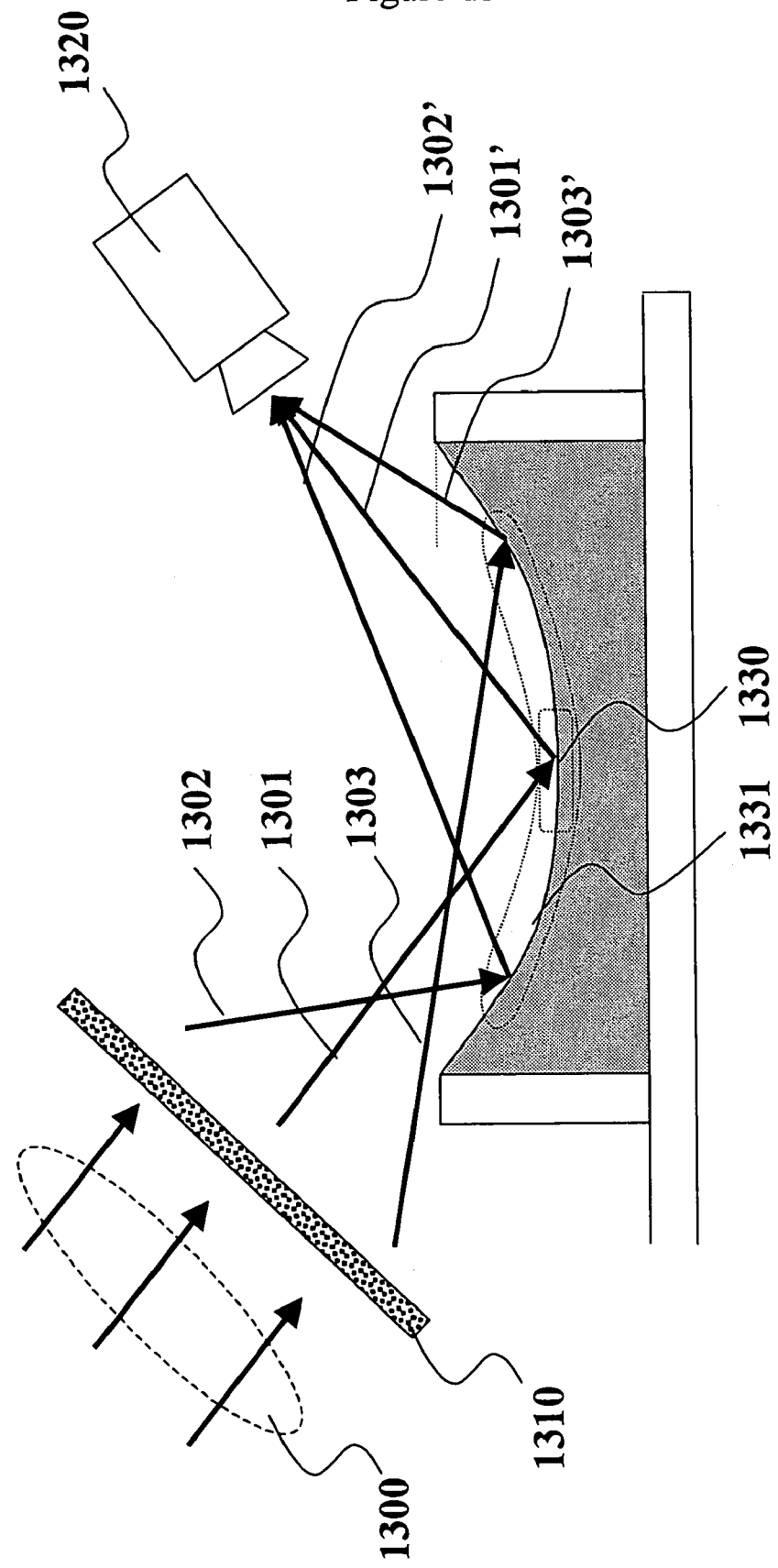
FIG. 13 is a schematic illustration indicating the effect by the lifting the diffusion ratio of the inspection light.

Firstly, the effect of the increase in diffusivity of the inspection light will be described with reference to FIG. 13. When any light diffusing means 1310 is not installed, the parallel light 1300 is incident on the liquid phosphor surface as the incoming light 1301 while being parallel, and only the reflected light 1301' is incident on an imaging means 1320. This means that, in this case, the imaging means 1320 captures only the reflected light from a surface 1330 completely flat with respect to the substrate surface. On the other hand, when the light diffusing means 1301 is installed, the parallel light 1300 is diffused by the light diffusing means 1310, and incident on the liquid phosphor surface as diffused lights 1301, 1302 and 1303 incident on the liquid phosphor surface at various angles, and the reflected lights 1301', 1302' and 1303' are incident on the imaging means 1320. This means, in this case, the imaging means 1320 captures the reflected light from an area 1331 including the surface completely flat with respect to the substrate surface and a part of the surface not flat thereto. Thus, the correlation between the surface shape and the brightness gets closer to the curve R by increasing the diffusivity of the inspection light.

Figure 14:
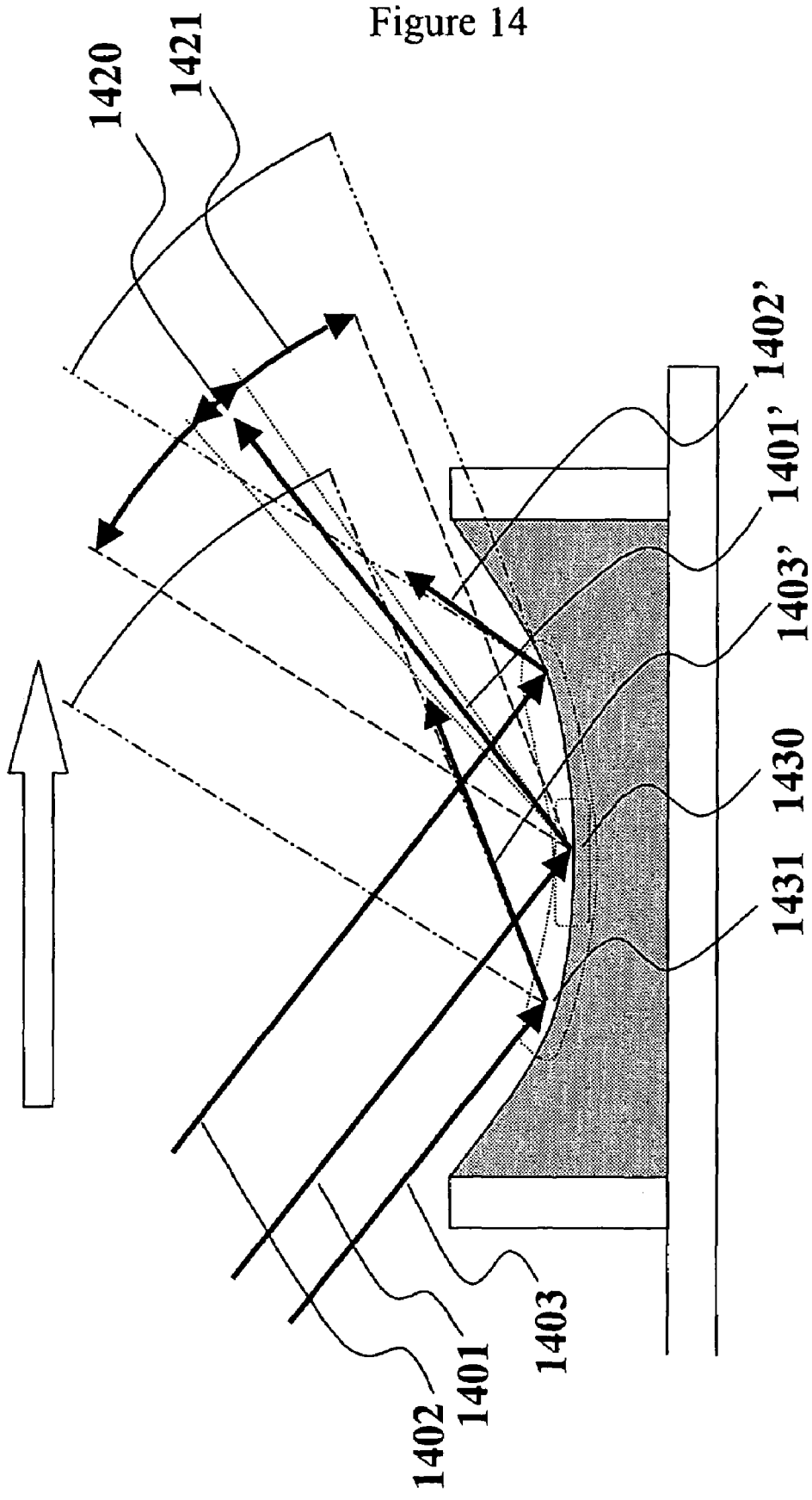
FIG. 14 is a schematic illustration indicating the effect by the lifting an aperture ratio of an imaging means.

Next, the effect of the increase in the image capture angular aperture of the imaging means will be described with reference to FIG. 14. When an image is captured by the image capture angular aperture 1420, the parallel lights 1401, 1402 and 1403 are incident on the liquid phosphor surface, and only the reflected light 1401' is reflected in the image capture angular aperture 1420. This means that, in this case, the image capture means captures only the reflected light from the surface 1430 completely flat with respect to the substrate surface. On the other hand, when an image is captured by the image capture angular aperture 1421, the parallel lights 1401, 1402 and 1403 incident on the liquid phosphor surface are reflected by the liquid phosphor surface, respectively to form the reflected light 1401', 1402' and 1403', and all of them are reflected in the image capture angular aperture 1421. This means that, in this case, the imaging means captures the reflected light from an area 1431 including the surface completely flat with respect to the substrate surface and a part of the surface not flat thereto. Thus, the correlation between the surface shape and the brightness gets close to the curve R by increasing the image capture angular aperture of the imaging means.

Generally speaking, if the image capture angular aperture is increased, the intensity of the light incident in the imaging means is also increased. If the light of the intensity not less than the capacity of a light receiving element of the imaging means is incident, measurement of high accuracy cannot be prospected. Thus, the imaging means is preferably provided with a received light intensity attenuating means.

It is also understood that reflectance is high on the liquid phosphor surface, and a light polarizing direction selecting means may be provided on an illuminating means, an imaging means, in order to improve the contrast of image.

In the above description, one liquid phosphor is taken as an example for easy understanding. However, in practice, a plurality of liquid phosphors must be inspected. To carry out the inspection on every liquid phosphor applied on the substrate, the brightness may be measured while relatively moving the position of the substrate to the incoming light in the direction across the groove formed in the substrate. Detailed configuration of the apparatus will be described below.

Firstly, in the conventional technology, the inspection on liquid phosphor is carried out on every liquid phosphor applied on the substrate as described above. As shown in FIG. 6, the brightness signal waveform 620 corresponding to the surface shape including the surface shape of liquid phosphor as shown in a graph 660 at, for example, the position of the dotted line s can be obtained. It is demonstrated that this brightness signal waveform 620 can be applied normally if corresponding to the surface shape of the substrate, large brightness signal and small brightness signal can be obtained from the grooves b and h including the liquid phosphor 600 and 602 with flat surface shape, and the grooves e and k including liquid phosphor 601 and 603 which are not applied normally, respectively, and brightness equivalent to that of the grooves e and k can be obtained from the grooves a, c, d, f, g, i, j and l without any liquid phosphor applied thereto, where the brightness peak of the part corresponding to the grooves to which liquid phosphor is applied, and the grooves to which liquid phosphor should be applied is denoted as 610, 611, 612 and 613, and hereinafter, referred to as the "brightness peak".

In the PDP, liquid phosphor is applied at the predetermined interval Lp, and the obtained brightness peaks 610, 611, 612 and 613 of the brightness signal waveform naturally appear at the predetermined periodical interval mLp (m: constant) corresponding to the application interval of liquid phosphor. Thus, the value of brightness peak from liquid phosphor applied to each groove on the substrate can be obtained by extracting the brightness peak at the point apart from the N-th brightness peak by the distance mLp as the (N+1)th brightness peak to the brightness waveform 620, and repeating this operation for every brightness peak. These values of the brightness peak are defined as the representative brightness for each groove, and the brightness peak waveform 640 can be obtained by successively arranging these values. The respective values 630, 631, 632 and 633 constituting the, brightness peak waveform 640 correspond to the liquid phosphor application volume for each groove, and the position of the groove and the application volume of liquid phosphor applied to the groove are specified by the brightness peak waveform 640. In addition, by setting an appropriate threshold 650 to the brightness peak waveform 640, the brightness peaks 631 and 633 below the threshold 650 are extracted, and the grooves corresponding to the brightness peaks 631 and 633 are specified to determine that the application volume of liquid phosphor applied to the grooves are out of the range of the predetermined value. This means whether or not the application volume of the applied liquid phosphor is in the range of the predetermined value is inspected to a part of the grooves to which every liquid phosphor is applied over the whole length in the longitudinal direction of the substrate, and NG (No Good) is determined to the substrate having the grooves out of the range of the predetermined value.

Figure 15:
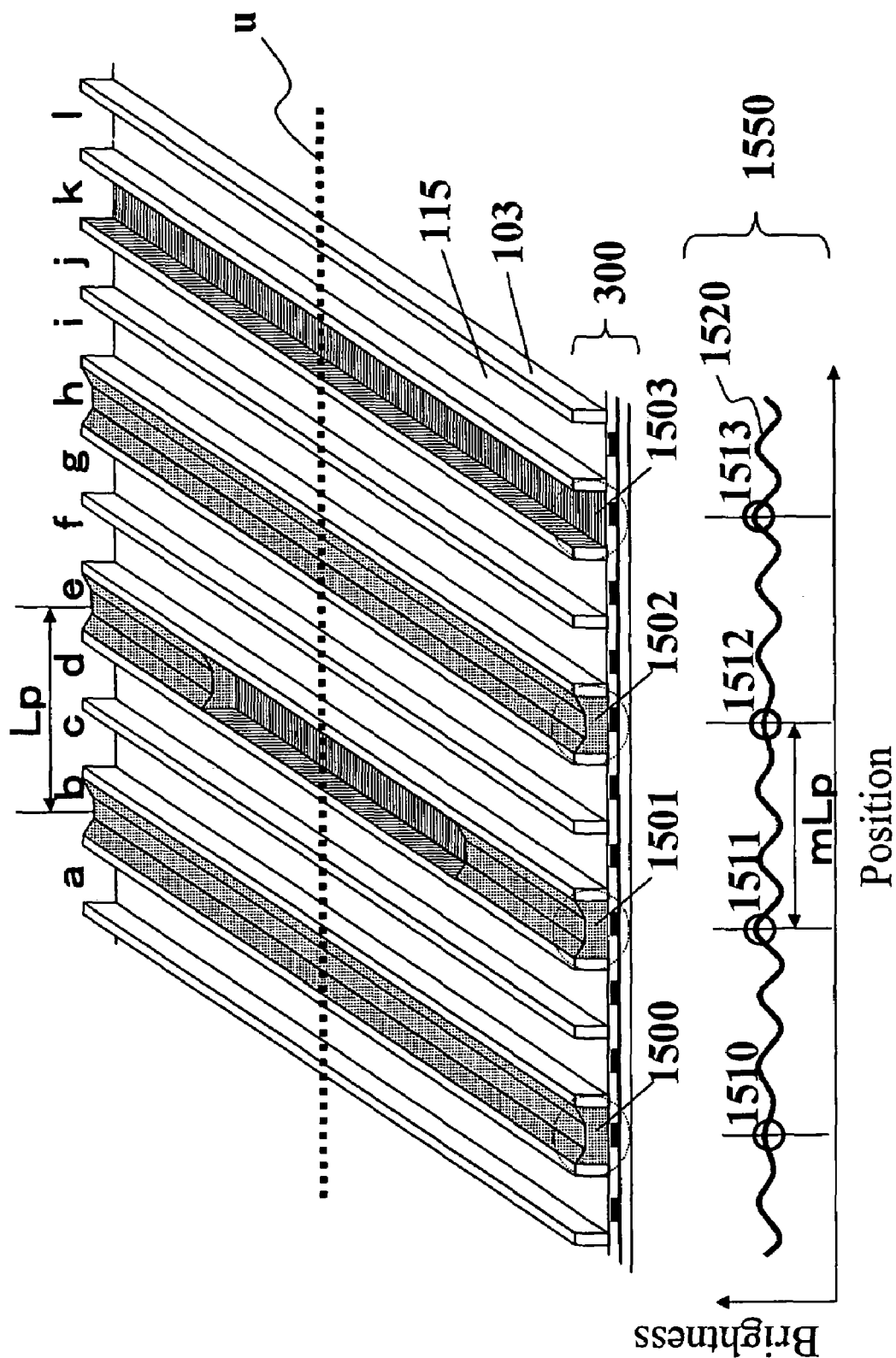
FIG. 15 is a schematic illustration indicating liquid phosphor applied to a substrate having grooves so that the surface shape is recessed, and the brightness signal waveform obtained by the inspection method of the present invention.

The method for carrying out the inspection of liquid phosphor to every liquid phosphor applied on the substrate using the conventional technology is as described above. However, when actually manufacturing substrates, liquid phosphor may be formed not with the application volume V2 for the flat surface, but with the application volume V1 for concave surface shape, or with the application volume V2 for convex surface shape. For example, when substrate is formed with the application volume V1, troubles when carrying out the inspection of the application state of liquid phosphor by the above conventional technology will be described with reference to FIGS. 9, 10 and 15. FIG. 15 is a schematic illustration showing liquid phosphor applied to the grooves and the brightness signal waveform obtained by the inspection method of the present invention.

As shown in FIG. 10, if the surface shape is concave, a part capable of reflecting the reflected light in the angular aperture is narrow, and the brightness of the reflected light obtained from liquid phosphor is apt to be increased. On the other hand, in the groove bottom part without any liquid phosphor applied thereto, the reflected light in the angular aperture is easily blocked by the partition walls. However, the reflecting surface is flat, and the reflectance is high as shown in FIG. 9, and the brightness of a certain degree can be obtained. As a result, no definite difference is present in the intensity of the reflected light from a liquid phosphor part to be inspected and a groove bottom part which need not be inspected as shown in the graph 1550 in FIG. 15, and it is difficult to extract the brightness signals 1510, 1511, 1512 and 1513 from the liquid phosphor part to be inspected. This means that the brightness peak waveform cannot be obtained easily.

Figure 16:
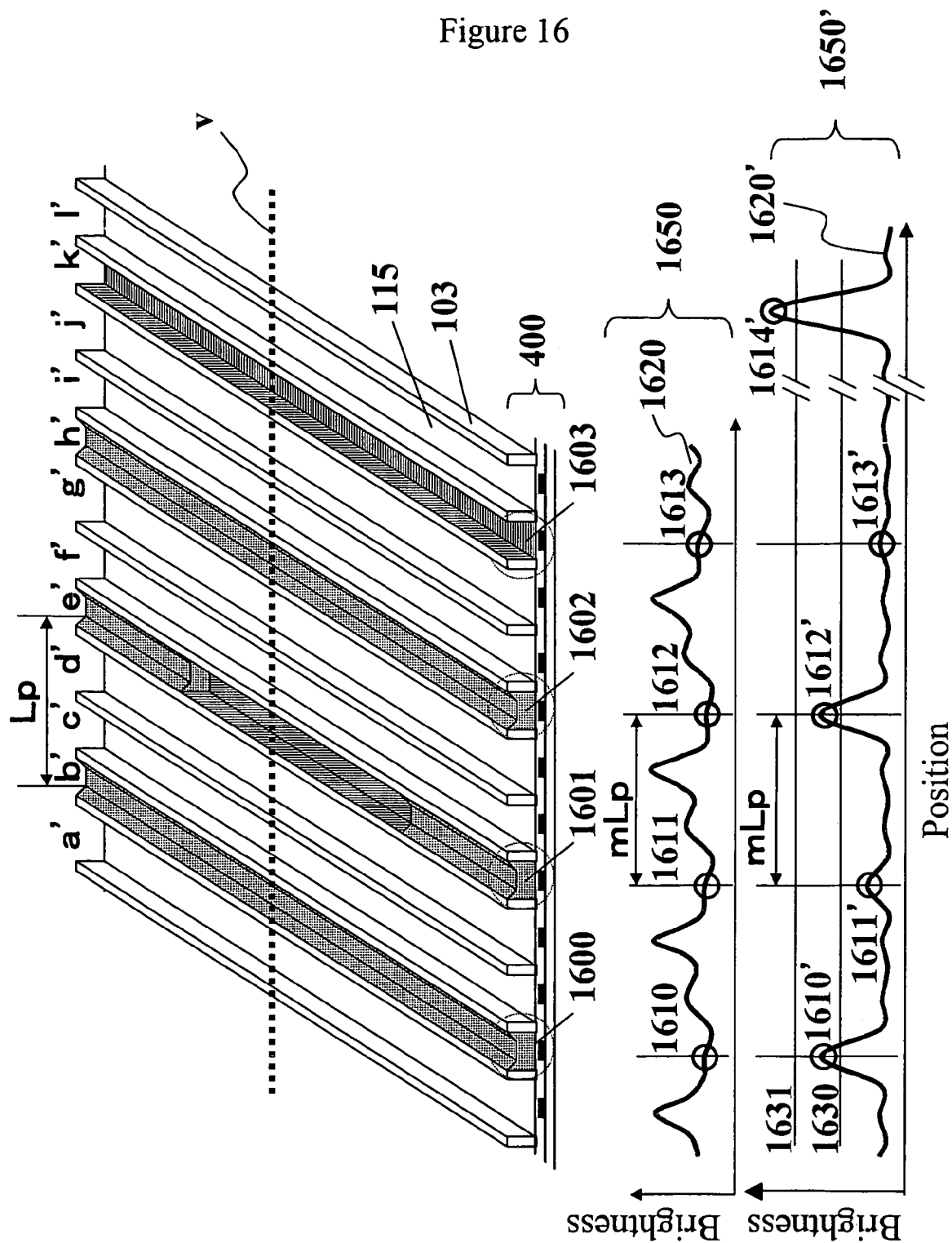
FIG. 16 is a schematic illustration indicating liquid phosphor applied to a substrate having grooves of three kinds of groove width so that the surface shape is recessed, and the brightness signal waveform obtained by the inspection method of the present invention.

In addition, this phenomenon raises a serious problem when inspecting the application state of liquid phosphor to the substrate comprising the grooves of at least two kinds of width as shown in FIG. 4. This problem will be described by using FIG. 16. FIG. 16 is a schematic illustration indicating liquid phosphor applied to the grooves and the brightness signal waveform obtained by the inspection method of the present invention. For example, in the substrate 400 in which three kinds of grooves with the groove depth satisfying the inequalities L<L<L are constituted orderly when inspecting the application state of liquid phosphor applied to the grooves b', e', h' and k' of the narrowest width L with the application volume smaller than the standard value, the intensity of the reflected light in the angular aperture from the liquid phosphor to be inspected will be considerably weakened due to the concave surface shape and the narrow groove width.

On the other hand, the reflected light in the angular aperture from bottoms of the grooves a', d', g' and j' of the widest width L3 is less easily blocked by the partition walls due to the large groove width, and the obtained intensity will be considerably increased. As a result, the reflected light brightness signal from liquid phosphor to be inspected is covered by the reflected light brightness signal from the groove bottom part as shown by the graph 1650 in FIG. 16. Thus, it is difficult to extract the brightness signals 1610, 1611, 1612 and 1613 from the liquid phosphor part to be inspected, and accurate measurement is impossible.

Here, the reflected light in the angular aperture brightness signal from the liquid phosphor to be inspected is defined as a signal (hereinafter, referred to as "S"), and the reflected light in the angular aperture brightness signal from the groove bottom part which need not be inspected is defined as the noise (hereinafter, referred to as "N"), and the S/N ratio is calculated. In the conventional technology, the S/N ratio is considerably decreased when the substrate manufacturing conditions such as the liquid phosphor application volume, the groove width, and the partition wall height are changed, the inspection cannot be carried out. This problem similarly occurs when manufacturing the substrate with the application volume V3 though there is a difference between concave and convex surface shapes of liquid phosphor.

The above problems are included in the conventional technology, and description will be made below on the inspection method of the present invention in order to solve these problems.

In order to increase the above S/N ratio, two methods, i.e., (1) to increase S and (2) to decrease N, are general, and the main point is placed in (2) to decrease N in the inspection method of the present invention. In the inspection method of the application state of liquid phosphor of the present invention, N means the reflected light in the angular aperture brightness signal from the groove bottom part which need not be inspected. In order to decrease this, the reflected light in the angular aperture from the groove bottom part may be captured.

A first effective method for obtaining the above effect includes the inspection at the angle of light incidence/reflection at which the reflected light in the angular aperture from the groove bottom part is completely blocked by the partition walls. The relationship between S and N in this inspection method will be successively described with reference to FIGS. 17, 18, 19 and 20. Here, FIGS. 17, 18, 19 and 20 are schematic illustrations showing the state of the reflected light reflected from the groove bottom surface or the liquid phosphor surface at the angle of light incidence/reflection θ or θ'. As already described above, when the light is captured, a light capturing means generally has a predetermined angular aperture, and the angular aperture θk will also be considered in the description of this technology.

Figure 17:
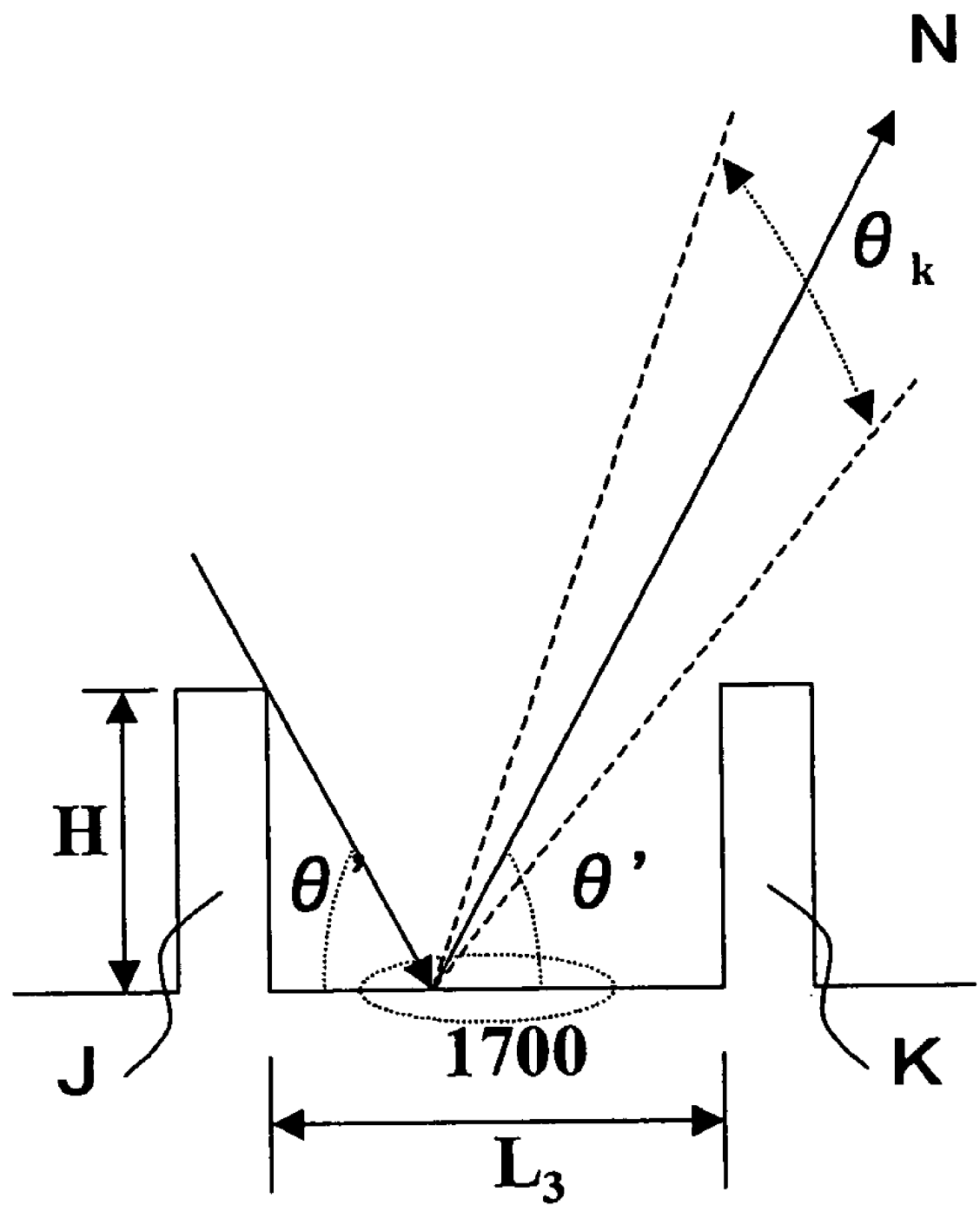
FIG. 17 is a schematic illustration indicating the state of the reflected light reflected in an angular aperture from a groove bottom surface at the angle of light incidence/reflection $\theta'$.
Figure 18:
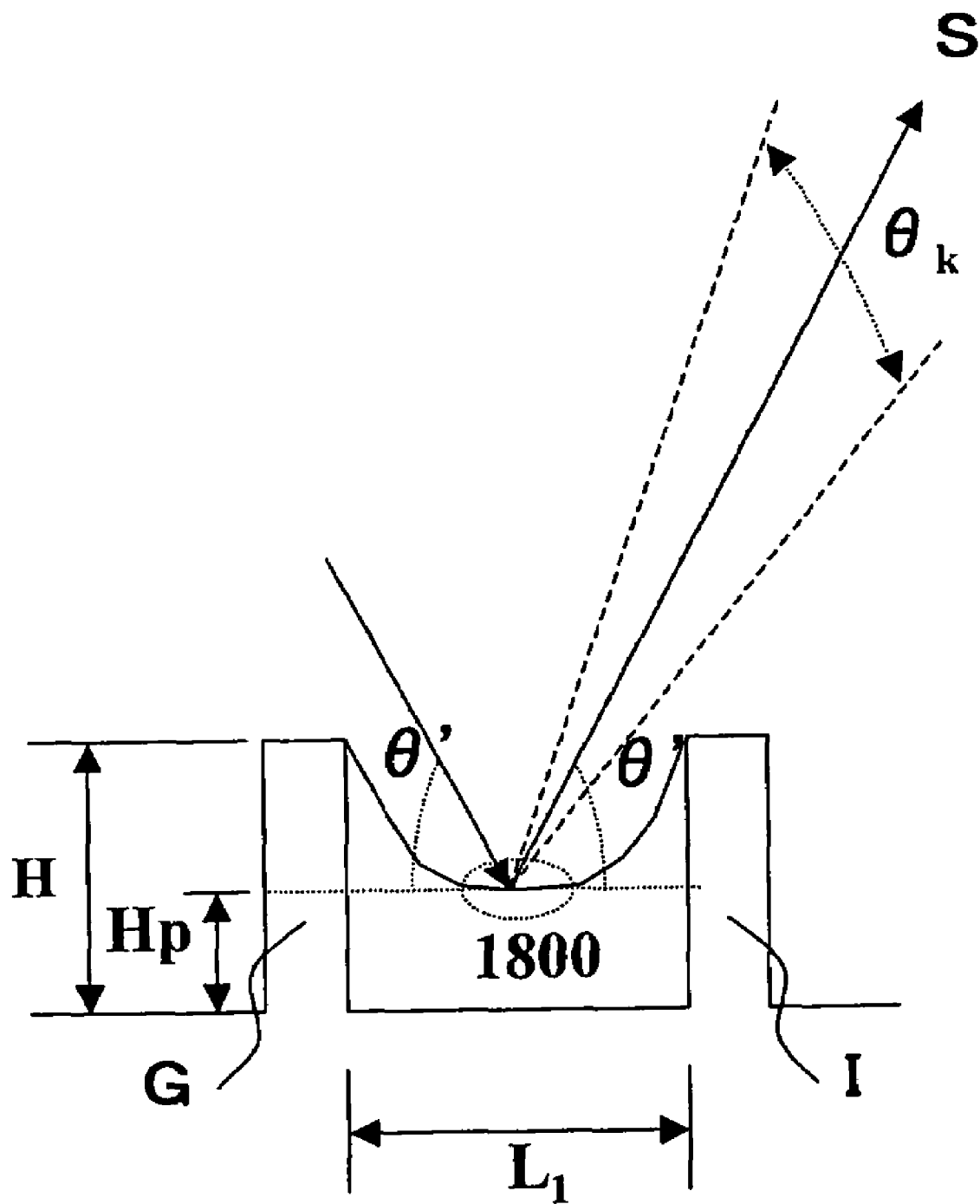
FIG. 18 is a schematic illustration indicating the state of the reflected light reflected in an angular aperture from the surface of liquid phosphor at the angle of light incidence/reflection $\theta'$.

Firstly, when the inspection is carried out at the angle of light incidence/reflection θ' as shown in FIG. 18, the reflected light S in the angular aperture is reflected at the part of 1800 in the range of the angular aperture θk. However, as shown in FIG. 17, at the angle of light incidence/reflection θ', the reflected light N in the angular aperture from the groove bottom part 1700 with the groove width L3(>L1) which need not be inspected can be captured. This means that a phenomenon shown by the upper graph in FIG. 7 occurs, the S/N ratio is considerably decreased, and the inspection with high accuracy is impossible.

Figure 19:
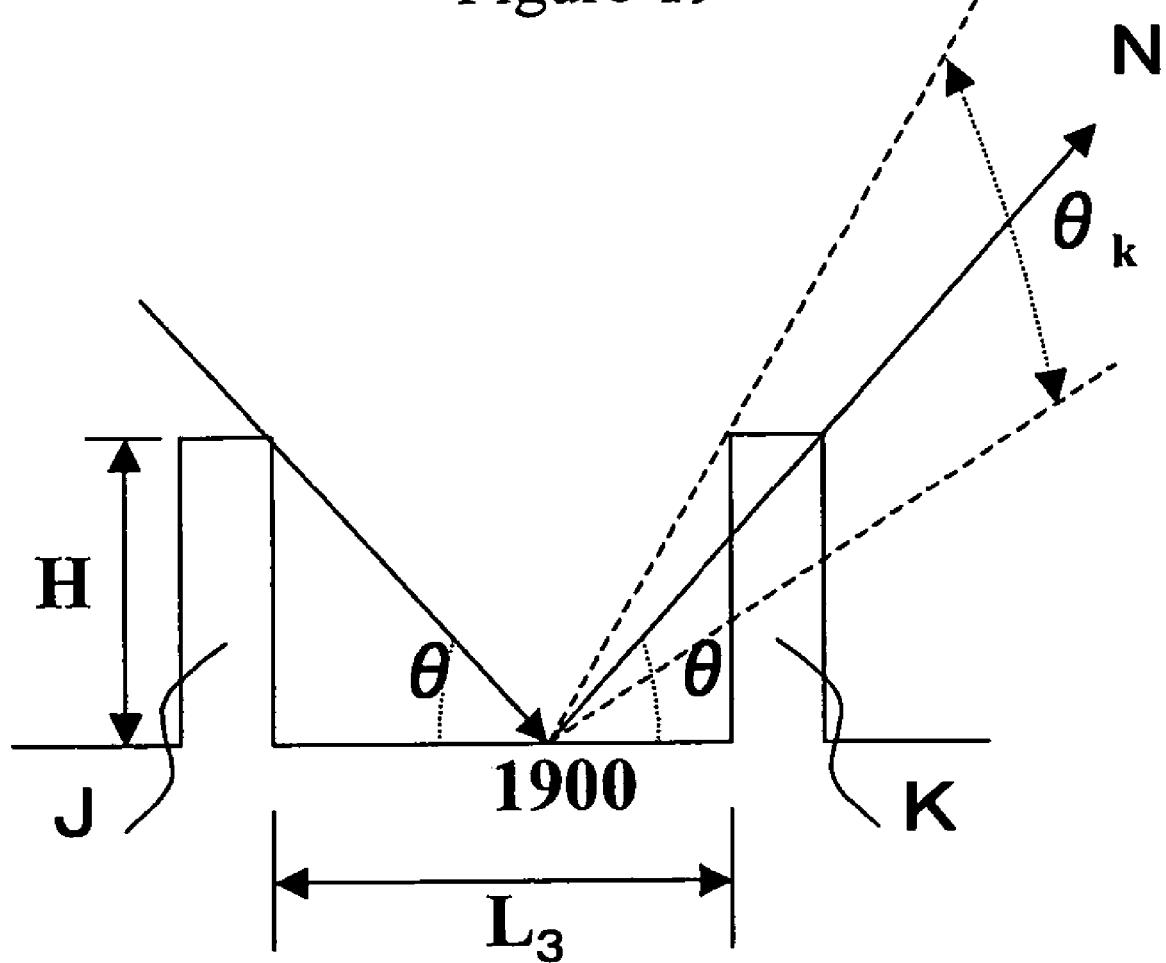
FIG. 19 is a schematic illustration indicating the state of the reflected light reflected in an angular aperture from the surface of the groove bottom at the angle of light incidence/reflection $\theta$.
Figure 20:
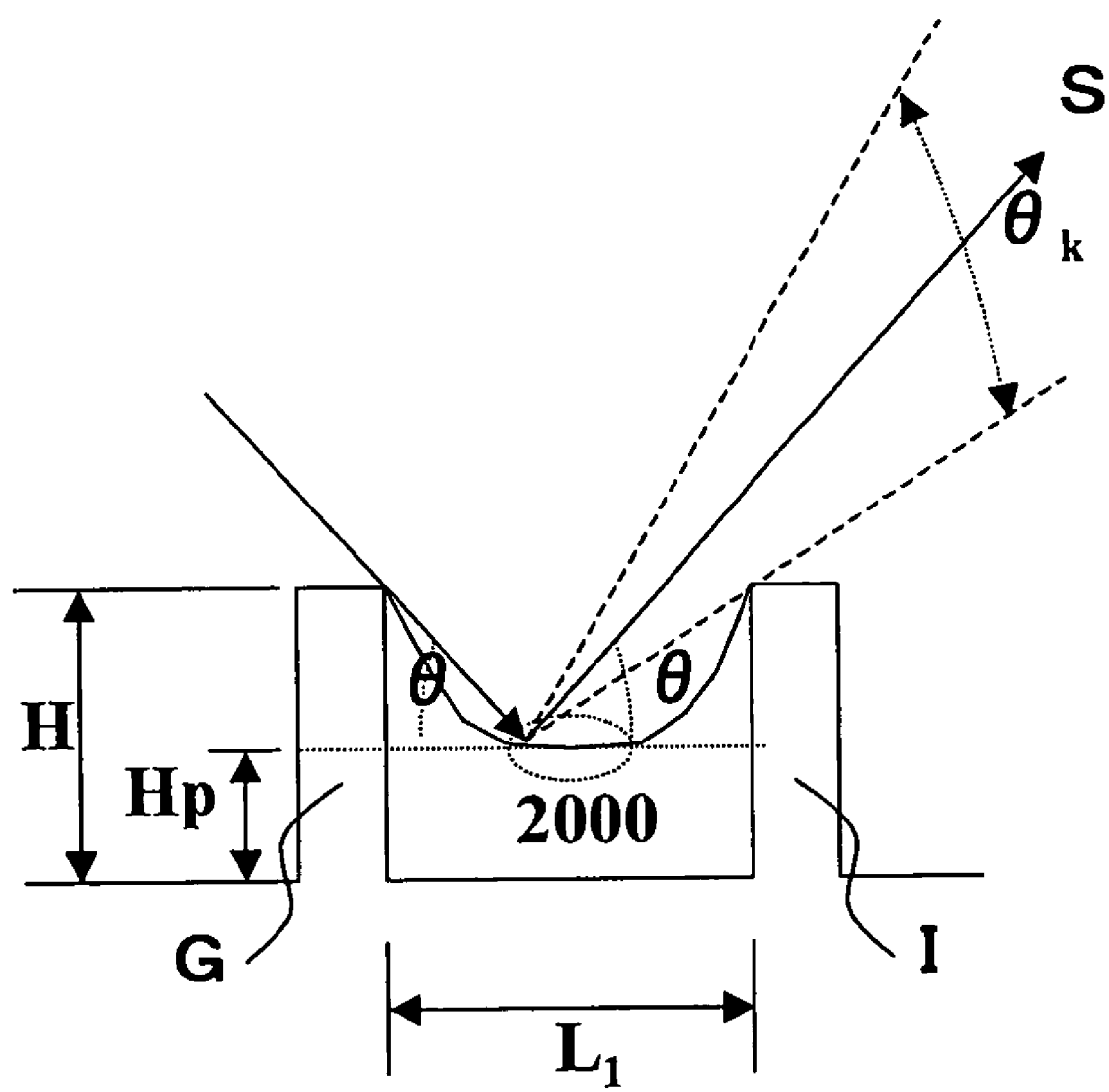
FIG. 20 is a schematic illustration indicating the state of the reflected light reflected in an angular aperture from the surface of liquid phosphor at the angle of light incidence/reflection $\theta$.

Next, description will be made on the inspection at the angle of light incidence/reflection θ. This method is characterized in that this angle of light incidence/reflection θ is determined so that the angular aperture θk at which the reflected light N in the angular aperture from the groove bottom part 1900 is captured is completely blocked by the partition wall K by the angular aperture θk, and the partition wall height H and the groove width L3 which are design values constituting the groove which need not be inspected. This means that the reflected light N in the angular aperture from the groove bottom part 1900 which need not be inspected is not captured at the angle of light incidence/reflection θ as shown in FIG. 19, and only the reflected light S in the angular aperture from liquid phosphor to be inspected can be captured as shown in FIG. 20. However, if the angle of light incidence/reflection θ is decreased excessively, the reflected light S in the angular aperture from the liquid phosphor surface to be inspected is blocked by the partition wall, and the S/N ratio is decreased. Thus, the inspection method of the present invention is characterized in that the angle of light incidence/reflection θ is determined so that the angular aperture θk for capturing the reflected light S in the angular aperture from the liquid phosphor surface 2000 is not blocked by the partition wall I by the angular aperture θk, and the partition wall height H, the groove width L1, and the surface height Hp of liquid phosphor to be applied which are design values constituting the groove to be inspected as shown in FIG. 20. The above concept is expressed by the formula 7 below.

[Angle at which S is not blocked by partition wall]
<θ<[angle at which N is blocked by partition wall]

As shown in FIGS. 19 and 20 as examples, the reflected light N in the angular aperture from the groove bottom part which need not be inspected is blocked by the partition wall by carrying out the inspection at the angle of light incidence/reflection θ determined by the formula 7, and the reflected light S in the angular aperture from the liquid phosphor surface to be inspected is received in the range of angular aperture θk. Thus, the brightness signal waveform 1620' as shown in the graph 1650' in FIG. 16 can be obtained, and the S/N ratio sufficient for carrying out the inspection with high accuracy can be obtained.

In order to identify a defect from the graph 1650' obtained from the above devises, an appropriate first threshold 1630 is set for the brightness signal waveform 1620' as described above, and the brightness peak 1611' and 1613' below the threshold may be detected. In the example in FIG. 16, a defect in that the application amount of liquid phosphor is smaller than the predetermined value is illustrated, and it is also possible to identify a defect in that the application amount of liquid phosphor is larger than the predetermined value. When the application amount of liquid phosphor is larger than the predetermined value, the surface shape of liquid phosphor gets close to the flat shape, and the brightness signal obtained from a defective part is larger than the brightness signal obtained from a normal part as described in FIG. 8. Thus, by setting an appropriate second threshold 1631, and detecting the brightness peak 1614' above this threshold, the defect that the application amount of liquid phosphor is larger than the predetermined value can be identified.

Description has been made above on the application state of liquid phosphor applied to the substrate with at least two kinds of groove width are orderly constituted as shown in FIGS. 4 and 16, and similar effect can be expected for the substrate constituted with equal groove width as shown in FIGS. 3, 5, 6 and 15.

Regarding the inspection of the application state of liquid phosphor applied to the substrate with at least two kinds of groove width orderly constituted as specifically shown in FIGS. 4 and 16, the angle of light incidence/reflection θ optimum for the inspection is determined by the formula 2 below, where H is the height of the partition wall forming the groove, $H_p$ is the surface height of phosphor, $L_\alpha$ is the width of the groove formed of the partition walls with phosphor applied thereto, and $L_\beta$ is the width of the groove formed of the partition walls without any phosphor applied thereto. Here, as an example, calculation is performed on the assumption that the angular aperture θk is 0° by stopping the diaphragm on the image capture side to the last.

$$\tan^{-1}\frac{2(H-H_p)}{L_\alpha} < \theta \leq \tan^{-1}\frac{2H}{L_\beta}$$

By carrying out the inspection at the thus-obtained angle of light incidence/reflection θ, the S/N ratio sufficient for carrying out the inspection with high accuracy can be obtained as described above. Further, as described above, in the calculation of the formula 2, assumption is made that the angular aperture θk is 0°, but in reality, the predetermined angular aperture θk capable of capturing the light without fail is present. Thus, if the sufficient S/N ratio is obtained in the actual inspection, the magnitude of the angular aperture θk can be considered in the formula 2.

In addition, the second method effective for decreasing N in order to improve the S/N ratio includes limitation of the wavelength of the inspection light to be 360 nm or under. As described above, the cause of generating N in the inspection signal is the incidence of the reflected light from the groove bottom part which need not be inspected, i.e., from the dielectric layer on the imaging means. The dielectric layer has a high glass component content, and glass has the optical characteristic of easily absorbing the light having the wavelength of 360 nm or under. Thus, by using the light having the wavelength of 360 nm or under in the inspection, the reflected light S from liquid phosphor can be obtained in an equivalent manner to that of the conventional technology while the reflected light N from the dielectric layer is decreased, and as a result, the S/N ratio is improved.

Figure 21:
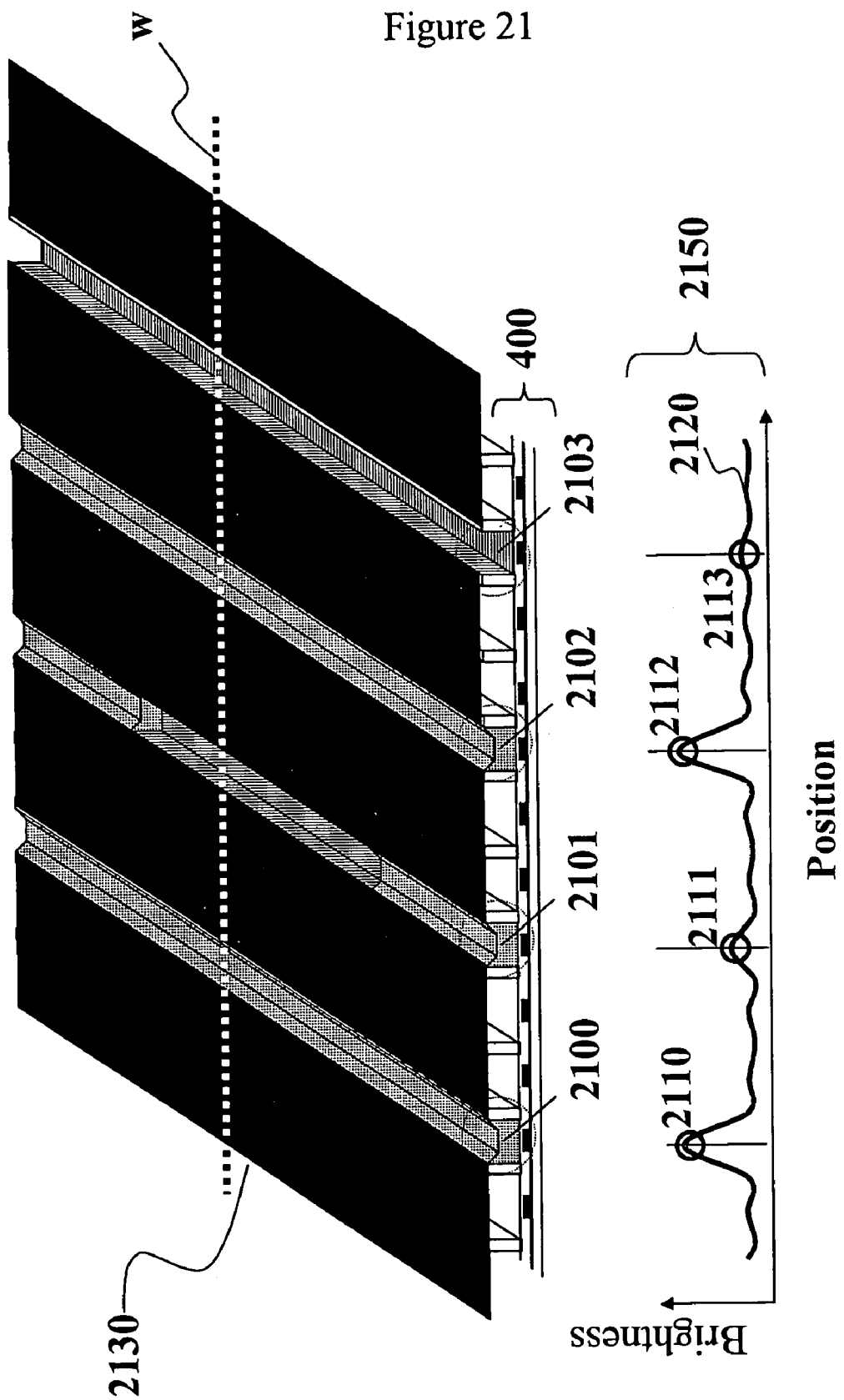
FIG. 21 is a schematic illustration of a mask for blocking the reflected light from grooves which need not be inspected.

The third method effective for decreasing N in order to improve the S/N ratio includes installation of the mask 2130 formed of a material of low light reflectance in the grooves which need not be inspected as shown in FIG. 21. As described above, the cause of generating N in the inspection signal is the incidence of the reflected light from the groove bottom part which need not be inspected on the imaging means. Thus, by covering the area for reflecting this reflected light N by the mask 2130 of low reflectance, only the reflected lights S 2110, 2111, 2112, and 2113 from the liquid phosphor 2100, 2101, 2102 and 2103 can be captured with high sensitivity, and the measurement signal waveform 2120 of high S/N ratio can be obtained.

The fourth method effective for decreasing N in order to improve the S/N ratio includes manufacture of the substrate to be inspected so as to facilitate the inspection of liquid phosphor. More specifically, the substrate is manufactured so as to satisfy the inequalities 6 given below, where H is the height of the partition walls forming the groove, and $H_p$ is the surface height of liquid phosphor.

$$0.6 < H_p/H < 0.9$$

By satisfying the inequalities 6, the reflected light S from liquid phosphor to be inspected is incident on the imaging means even when the angular aperture of the imaging means is sufficiently wide so as to improve the inspection sensitivity, the reflected light N from the groove bottom part which need not be inspected is blocked by the partition walls, and the angle of light incidence/reflection θ at which the light is not incident on the imaging means can be easily set. In addition, if the height H of the partition walls is equal to the surface height $H_p$ of liquid phosphor, the intensity of the reflected light S from liquid phosphor to be inspected becomes too high by the principle of the inspection method of the present invention described above, and the light of the intensity exceeding the capacity of the light receiving element provided on the imaging means is incident on the light receiving element, and measurement of high accuracy cannot be expected.

The fifth method effective for decreasing N in order to improve the S/N ratio includes coating of a fluorescent layer successively from the widest groove when manufacturing the substrate 310 constituted of the grooves of at least two kinds of the width as shown in FIGS. 4 and 16. As described above, a problem in that the S/N ratio in the inspection is degraded considerably occurs when the reflected light from the dielectric layer of the groove of large groove width is incident on the imaging means when inspecting liquid phosphor applied to the groove of the small groove width in the substrate 310 constituted of the grooves of at least two kinds of the width. Thus, the fluorescent layer is first coated on the groove of the large groove width, and if liquid phosphor is inspected, the reflected light S from liquid phosphor to be inspected is incident on the imaging while the reflected light N from the groove bottom part of the small groove width which need not be inspected is blocked by the partition walls, and the angle of light incidence/reflection θ which is not incident on the imaging means can be easily set. In addition, when carrying out the inspection of liquid phosphor applied to the groove of the small groove depth, the dried fluorescent layer is already coated on the groove of the large groove width, and since this fluorescent layer is lower in reflectance than the dielectric layer, the reflected light N from the groove which need not be inspected is decreased when inspecting liquid phosphor, and the S/N ratio is improved.

In addition, the inspection method of the present invention is characterized in that the imaging means has a plurality of light receiving elements arrayed in a one-dimensional manner, this light receiving element is disposed in the direction orthogonal to the direction of relative movement of the substrate to be inspected to the optical system, i.e., in the same direction as the groove formed on the substrate, the reflected light from liquid phosphor is captured with the predetermined width, and the intensity signal is used in the inspection of liquid phosphor as two-dimensional image information. In addition, the signal processing means in the inspection method of the present invention is characterized in that brightness information for a plurality of light receiving elements is added to image information obtained by the imaging means, and averaged in the arranging direction of the light receiving elements, and the average brightness signal waveform can be obtained by using the average value.

By replacing this average brightness signal waveform by the above brightness signal waveform 660, etc. and performing similar processing thereafter, the application volume of liquid phosphor applied to the substrate shown in FIG. 5 can be measured with high accuracy. This processing will be described with reference to FIGS. 5 and 22.

As described above, the substrate 320 shown in FIG. 5 has the groove 119 having transverse ribs, which is different from the substrates 300 and 310 shown in FIGS. 3 and 4. When liquid phosphor is applied to the groove 119 having transverse ribs, liquid phosphor 2201, 2202, 2203 and 2204 is applied with different application volume for each of a plurality of cells 120 since the viscosity of liquid phosphor is relatively higher than that of water, etc. However, when the brightness signal waveform is obtained by paying attention to only one pixel in the light receiving element of the imaging means immediately after applying liquid phosphor, the quantity of light captured by the light receiving element becomes the representative value indicating the application volume of liquid phosphor applied to the groove having transverse ribs, and the application volume of the total liquid phosphor cannot be measured correctly if tried. This indicates that, if the reflected light from the liquid phosphor 2204 applied so that, for example, the surface shape of one pixel in question is incidentally concave is captured at the position of the dotted line x, the brightness signal waveform 2220 indicated by the graph 2250 is obtained to determine that the total application volume of the applied liquid phosphor is small, and if the reflected light from the liquid phosphor 2201 applied so that, for example, the surface shape of one pixel in question is incidentally flat is captured at the position of the dotted line x', the total application volume of the applied liquid phosphor is the value for exactly filling a space between the part walls.

To prevent this, and to more correctly measure the total application volume of liquid phosphor applied to the groove 119 having transverse ribs, the reflected light from the applied liquid phosphor is captured for sufficiently large number of cells, and the brightness thereof may be averaged to obtain the representative value indicating the application volume of the applied liquid phosphor. More specifically, brightness information for a plurality of light receiving elements is added in the arranging direction of the light receiving elements for image information obtained by the imaging means, and averaged for the width y between the dotted lines x-x' in FIG. 22, and processing for obtaining the average brightness signal waveform 2221 indicated by the graph 2260 by using the average value may be performed. In addition, this method can naturally be used in the measurement of the application volume of liquid phosphor applied to the grooves 115, 116, 117 and 118 having no transverse ribs.

In the above description, it is assumed that each of a part of every liquid phosphor applied to the grooves on the substrate is inspected in the direction across the grooves formed in the substrate as the representative for each groove which is the object to be inspected. However, liquid phosphor is preferably inspected over the entire surface of the substrate by using methods such as (1) of increasing the view field of the imaging means, (2) of increasing the number of imaging means, and (3) of carrying out a plurality of inspections while changing the view field of the imaging means to one substrate to be inspected.

In addition, the inspecting means of the present invention has a means of measuring the moving speed of the substrate, and is characterized in that the application volume of each liquid phosphor can be measured with high accuracy without being influenced by the variance in the substrate moving speed. The liquid phosphor application volume can be measured correctly even by using a relatively inexpensive substrate carrying means with variance in the substrate carrying speed without using any expensive substrate carrying means capable of carrying the substrate at the predetermined speed by measuring the substrate moving speed, and reflecting the obtained result in the measurement of the liquid phosphor application volume for each groove. Further, the means for measuring the substrate moving speed of the present invention does not require any special facility, but is capable of measuring the substrate moving speed by the brightness signal obtained to measure the liquid phosphor application volume, resulting in no waste of the cost.

Figure 23:
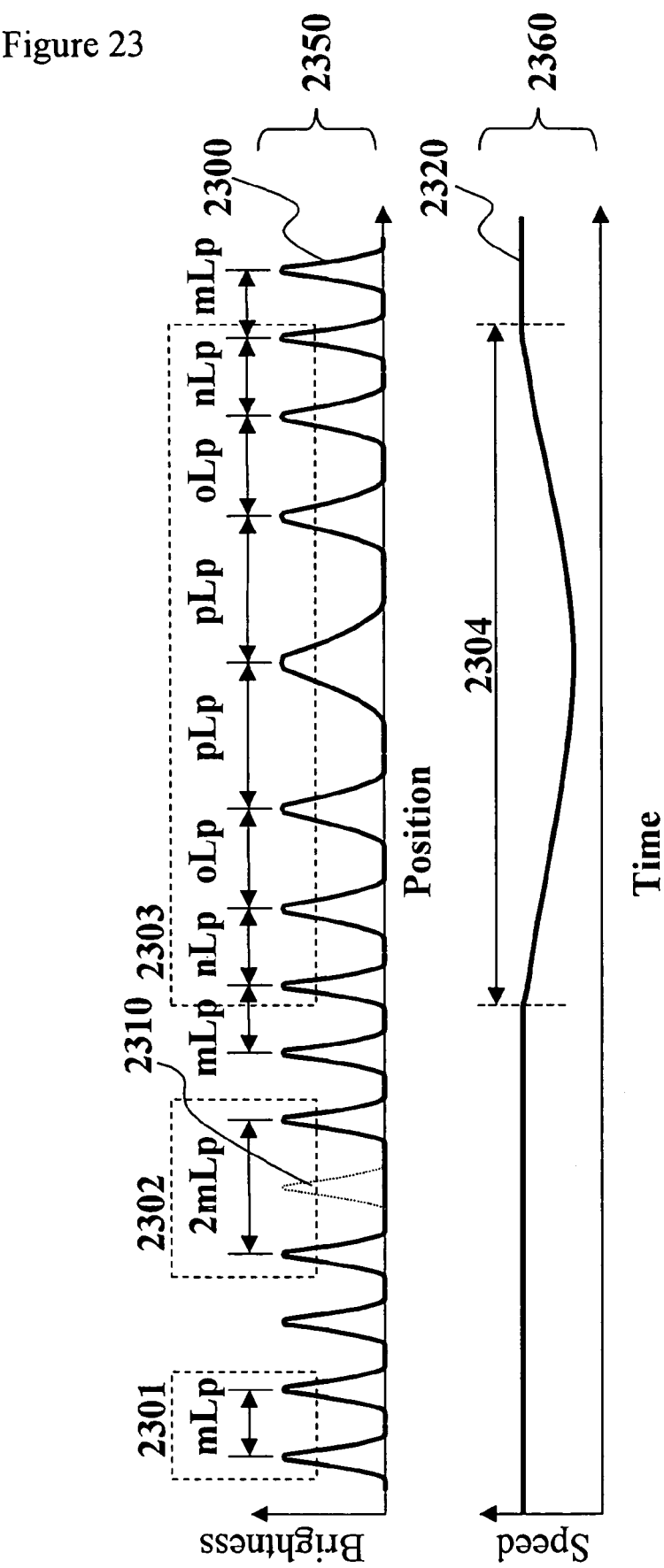
FIG. 23 is a schematic illustration indicating the relationship between brightness signal waveform obtained by the inspection and the substrate carrying speed.

Troubles when the substrate moving speed is fluctuated and specific remedies therefore will be described with reference to FIG. 23.

As described above, in the PDP, the fluorescent layer is formed at the predetermined interval Lp. It is assumed here that the substrate carrying speed is constant. The brightness peak of the obtained brightness signal waveform naturally appears at the periodic interval mLp (m: constant) corresponding to the space of liquid phosphor. If assuming that the substrate carrying speed is not constant, the brightness peak of the obtained brightness signal waveform appears at the interval different from the interval mLp to the interval Lp of liquid phosphor. If the above operation is considered in the reverse direction, it is understood that the substrate moving speed can be measured by measuring the interval of the brightness peaks. In addition, it is concluded that, if the interval of the brightness peaks is constant, the substrate carrying speed is also constant, and if the interval of the brightness peaks is in variance, the substrate carrying speed is also in variance.

A case will be considered below in that troubles occur in the means for applying liquid phosphor to the grooves, for example, no liquid phosphor is applied to a certain groove, or liquid phosphor of the amount below the predetermined value is applied, but the intensity of the reflected light is low. In such a case, the reflected light from liquid phosphor is not extracted as the brightness peak, and the interval of the brightness peaks is different from the predetermined interval mLp similar to the above case in which the substrate carrying speed is changed.

As described above, in the extraction of the brightness peaks, the brightness peak at the point apart from the N-th brightness peak by the distance mLp for the brightness waveform is extracted as the (N+1)-th brightness peak, and these operations are repeated for all brightness peaks. Thus, if the distance between the brightness peaks is not mLp, the. (N+1)-th brightness peak cannot be recognized. Two kinds of determination are considered in this case; one is that the appearing position of the brightness peak is deviated because the substrate moving speed is changed, and the other one is that the brightness peak cannot be extracted because no liquid phosphor is applied or the liquid phosphor application volume is small. The latter is attributable of defects of the substrate which is an object to be inspected, and NG must be determined naturally. However, in the former, no defective parts are present in the substrate itself, and it will be a mistaken detection if NG is determined here. This means that, when the interval of the brightness peaks is different from the predetermined interval mLp, it is necessary to correctly determine whether or not the difference is attributable of any defect of the substrate, or the variance in the substrate carrying speed. For this purpose, the substrate carrying speed is measured, and defects of the substrate may be determined if the moving speed is not changed, or no defects of the substrate may be determined if the substrate moving speed is changed.

Here, a specific method for measuring the substrate carrying speed will be described with reference to FIG. 23. Firstly, it is understood that, when the substrate carrying speed is fluctuated, e.g., when the speed is suddenly reduced, the brightness peak interval is changed at random in the brightness signal waveform 2300 indicated by the graph 2350 in FIG. 23 as shown by 2303, and a plurality of brightness peaks are continuously influenced (n, o and p: constant). On the other hand, when no liquid phosphor is applied, or when the brightness peak for the groove cannot be extracted because the application volume is small, the apparent brightness peak interval 2302 becomes integral multiple of the predetermined interval mLp. By utilizing these two different characteristics, whether or not any defective part is actually present when the interval between the brightness peaks is other than mLp. This means that there is a defective part 2310 if the brightness peak interval is integral multiple, the substrate is determined NG regarding the acceptance/rejection thereof. On the other hand, if at least one of two conditions that the brightness peak interval is not integral multiple of mLp, and that the intervals of the plurality of brightness peaks are continuously influenced is established, it is determined that no defective part is present in the substrate though the substrate carrying speed is fluctuated during the image capture of the part. By introducing this signal processing method, presence/absence of any defect can be determined even with the variance in the substrate carrying speed. For the convenience of the description, description is made only for the case in which the substrate carrying speed is suddenly reduced, but this method is also applicable even when the substrate carrying speed is suddenly increased.

As described above, the method for calculating the substrate carrying speed by the signal obtained for measuring the liquid phosphor application volume as a means for measuring the substrate carrying speed for realizing an inexpensive device. As a matter of course, an exclusive facility for measuring the substrate carrying speed is installed for the substrate moving speed measuring means, and the obtained substrate carrying speed information is input in the signal processing means so as to be reflected in the measurement of the liquid phosphor application volume for each groove. In this case, when the distance between the brightness peaks is other than the interval mLp, the substrate carrying speed information as indicated by the graph 2360 in FIG. 23 obtained by the substrate moving speed measuring means is referred to. If the moving speed is not changed, it is determined that the defective part 2310 is present in the substrate. If the substrate moving speed is changed as shown by 2304, it may be determined that no defective part is present in the substrate. The case in which there is variance in the substrate carrying speed is indicated. However, the inspecting means of the present invention can be realized by moving at least one of the illuminating means and the imaging means, and the substrate to be inspected. If variance in speed is present in the moving means for each of them, the above speed corrective method will be an effective means.

Description is made above on the inspection method in the phosphor inspection step (I). 252 of the present invention. Description will be made below on the inspection method in the phosphor inspection step (II) 254 with reference to FIGS. 24, 25 and 26.

Figure 24:
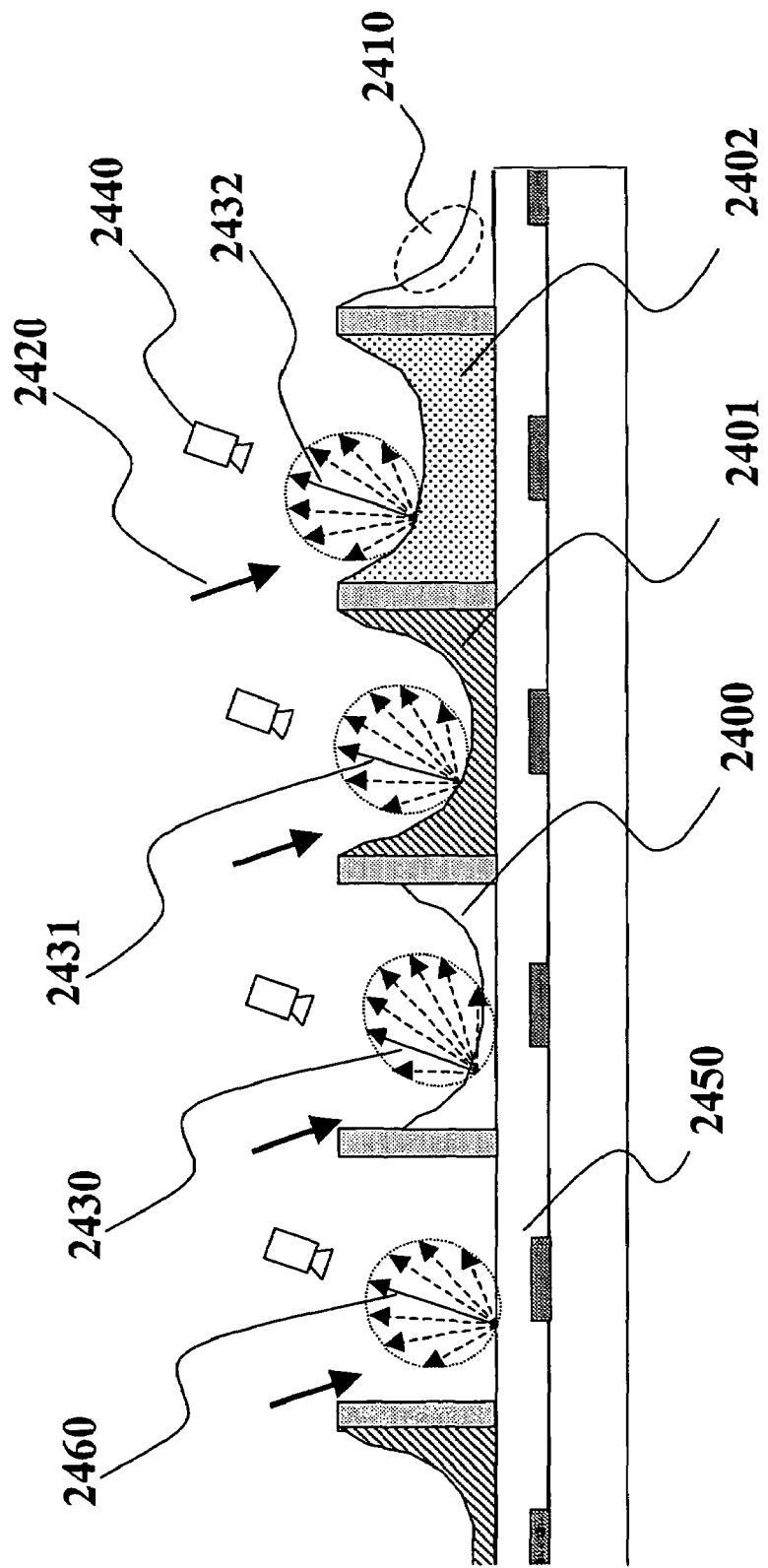
FIG. 24 is a schematic illustration indicating the principle of the inspection of a fluorescent layer by the reflected light.

At the time of the phosphor inspection step (II) 254, a dried fluorescent layer (hereinafter, referred to as "fluorescent layer") is formed on the groove constituted of the partition walls. The fluorescent layer is formed of fine particles mainly consisting of fluorescent material in a coagulated manner, and a large number of fine uneven parts are formed on the surface of the layer. When the state of this fluorescent layer is inspected by the conventional technology, the incoming light 2420 is allowed to be incident on a skirt 2410 with heavy changes of the amount of phosphor as shown in FIG. 24, and the reflected light from the skirt 2410 is captured by the imaging means 2440. However, as shown in FIG. 24, the light scattering by the surface of the fluorescent layer is drastic as shown in FIG. 24, and the difference in brightness is small between the scattering light 2431 incident on the imaging means 2440 from the fluorescent layer 2401 with the standard amount of phosphor, the scattering light 2430 incident on the imaging means 2440 from the fluorescent layer 2400 with the amount of phosphor less than the standard value, and the scattering light 2432 incident on the imaging means 2440 from the fluorescent layer 2402 with the amount of phosphor larger than the standard value. Further, when any fluorescent layer is not formed due to defects, the incoming light is reflected by the dielectric layer 2450. The dielectric layer is formed of fine particles mainly consisting of glass powder in a coagulated manner, a large number of uneven parts are formed on the surface thereof similar to the fluorescent layer, and the light scattering occurs thereby, and the scattering light 2460 is incident on the imaging means 2440. This means that, in the conventional technology, the change in the image capture brightness is small to the change in the shape of the fluorescent layer as indicated by the curve U in FIG. 26, and measurement with high accuracy is difficult.

As described above, the phosphor used in the PDP is excited to emit light by irradiating ultraviolet rays. The intensity of emission is influenced by the amount of phosphor at the part subjected to irradiation of ultraviolet rays and higher as the amount of phosphor is larger, and the intensity of emission is lower as the amount of phosphor is smaller.

Figure 25:
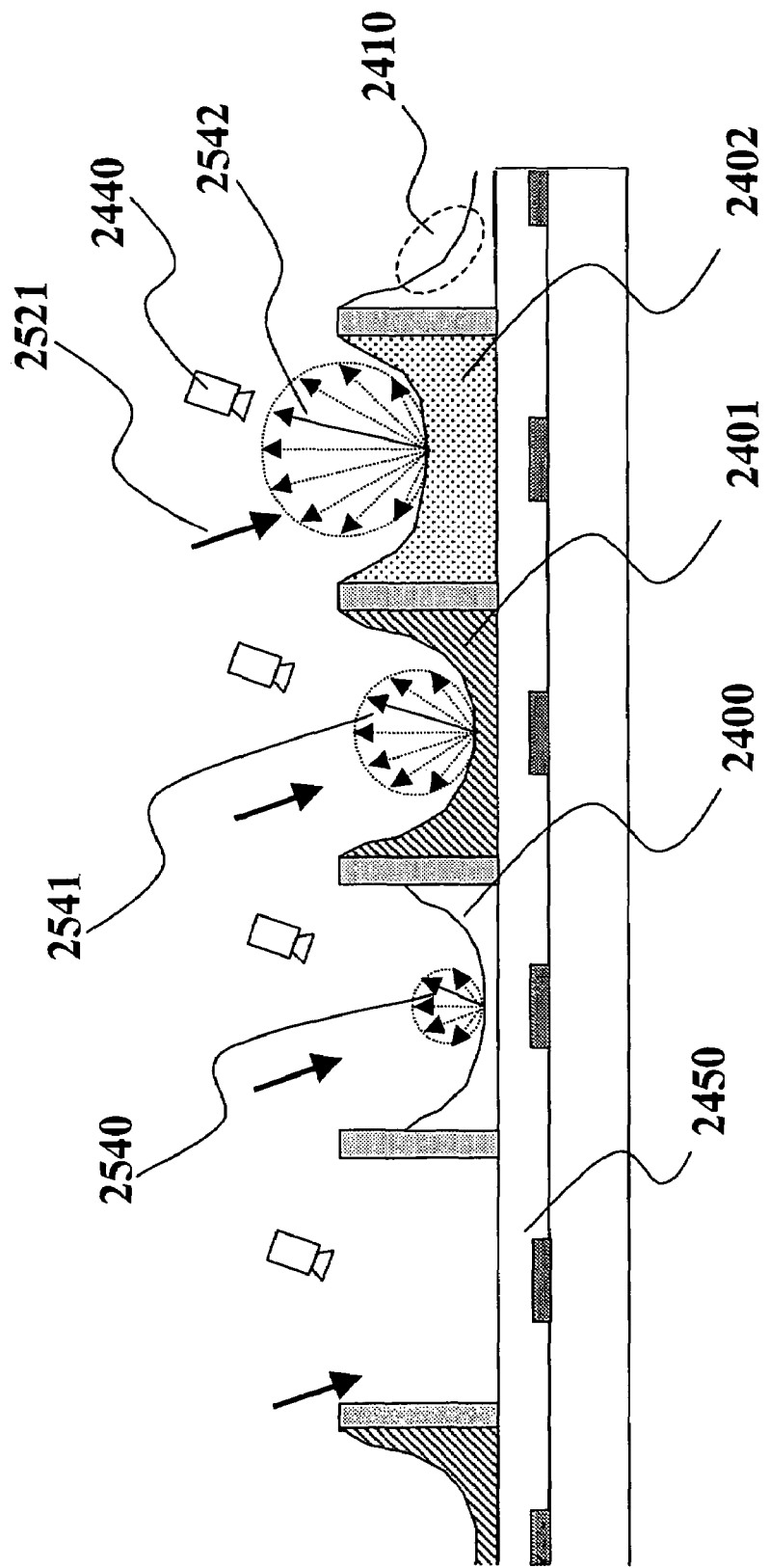
FIG. 25 is a schematic illustration indicating the principle of the inspection of a fluorescent layer by fluorescent photogenesis.
Figure 26:
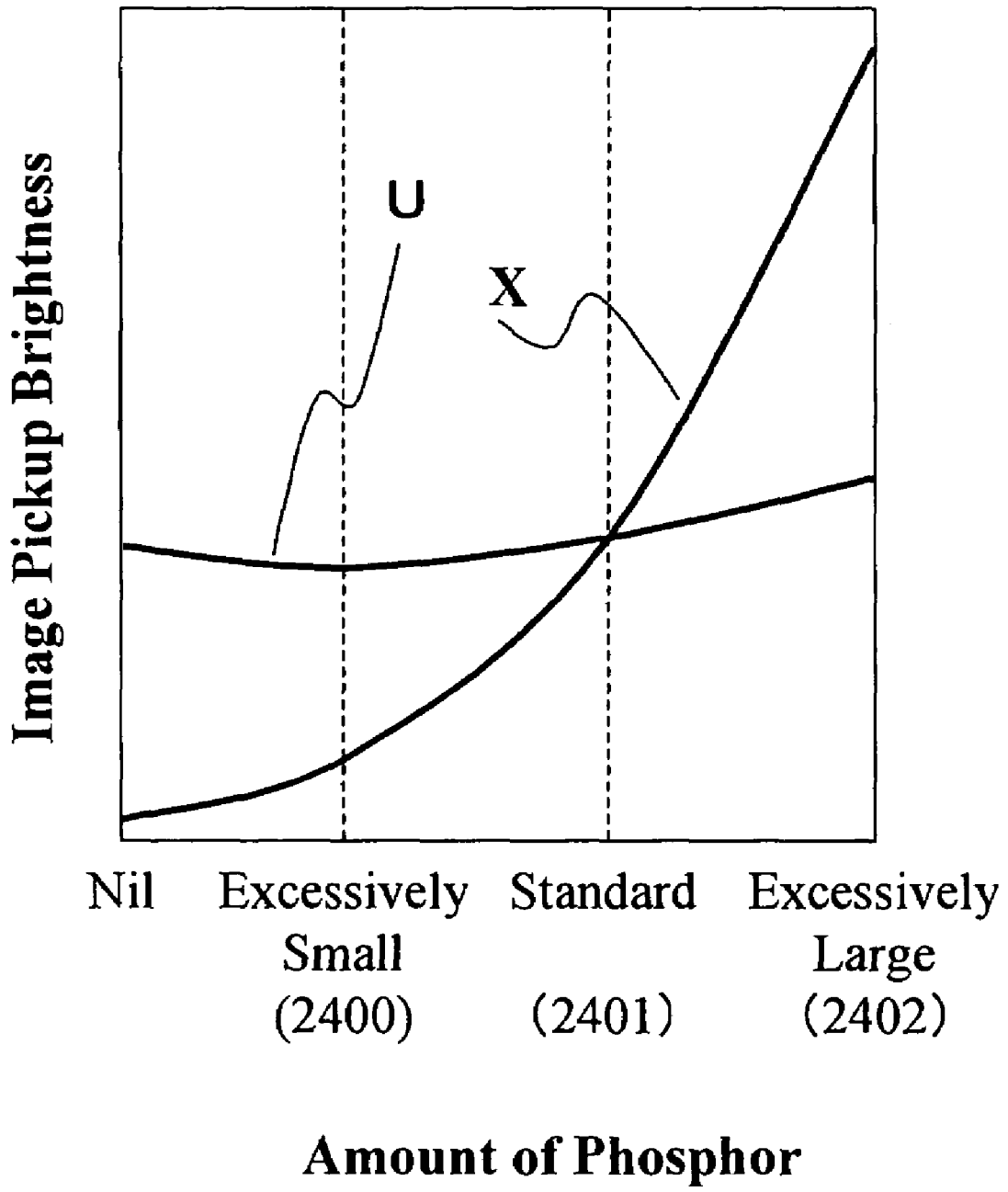
FIG. 26 is a schematic illustration indicating the relationship between the amount of phosphor applied to grooves and the intensity of fluorescent photogenesis.

The inspection method of the present invention utilizes this principle. As shown in FIG. 25, when the fluorescent layer is irradiated with the light 2521 of the wavelength of 260 nm or under for promoting the fluorescence as shown in FIG. 25, the intensity of the fluorescent photogenesis is different according to the amount of phosphor. Thus, the brightness of fluorescent photogenesis 2540, 2541, and 2542 incident on the imaging means 2440 is higher as the amount of phosphor is larger, and lower as the amount of phosphor is smaller as indicated by the curve X in FIG. 26. When no fluorescent layer is formed due to any defects, no fluorescent photogenesis is generated, and the image capture brightness becomes much lower. This means that, in the inspection method of the present invention, the amount of phosphor is measured by utilizing the relationship between the amount of phosphor and the intensity of fluorescent photogenesis to determine non-defective or defective products.

In the above, description is made on a substrate model with four fluorescent layers of different amount of phosphor adjacent to each other as an example for easy understanding. However, in practice, a plurality of fluorescent layers must be inspected. In order to carry out the inspection of all phosphors formed on the substrate, the brightness of the fluorescent photogenesis may be measured while relatively moving the position of the substrate with respect to the incoming light in the direction across the grooves formed on the substrate. Detailed configuration of the device will be described below.

As described above, the inspection of the fluorescent layer is carried out for every fluorescent layer applied on the substrate to obtain the brightness signal waveform 720 corresponding to the amount of phosphor of fluorescent layer as indicated by the graph in FIG. 7. This brightness signal waveform 720 is formed normally if corresponded to the part of the fluorescent layer of the substrate, the large brightness signal and the small brightness signal are obtained from the grooves b and h including the fluorescent layers 700 and 702 with the standard amount of phosphor, and from the grooves e and k including the fluorescent layers 701 and 703 which are not normally applied, respectively, and it is shown that equivalent brightness from the groove k can be obtained from the grooves a, c, d, f, g, i, j and l having no fluorescent layer formed thereon. Here in the brightness signal waveform 720, the peak of the brightness of a part corresponding to the position of the groove in which the fluorescent layer is formed or should be formed are referred to as 710, 711, 712 and 713, respectively, and hereinafter, referred to as "brightness peak".

No fluorescent layer is formed on the grooves a, c, d, f, g, i, j and l, yet. But in some cases, the fluorescent layer with another color or other two colors thereon have already been formed due to the convenience of the step. In such cases, in order to carry out the inspection by paying attention to only a certain color to be inspected, a captured image wavelength selecting means is provided on the imaging means, and the inspection is carried out for the color to be inspected.

Acceptance/rejection of the substrate to be inspected can be determined by performing the signal processing similar to that of the waveform obtained by the inspection method in the phosphor inspection step (I) 252 of the present invention to the emission brightness signal waveform obtained by the above inspection method. In addition, the method for detecting any defects with high accuracy by using the above substrate carrying speed can also be applied.

An inspection device for realizing the inspection method and the manufacturing method of the present invention will be described with reference to FIG. 27.

Figure 27:
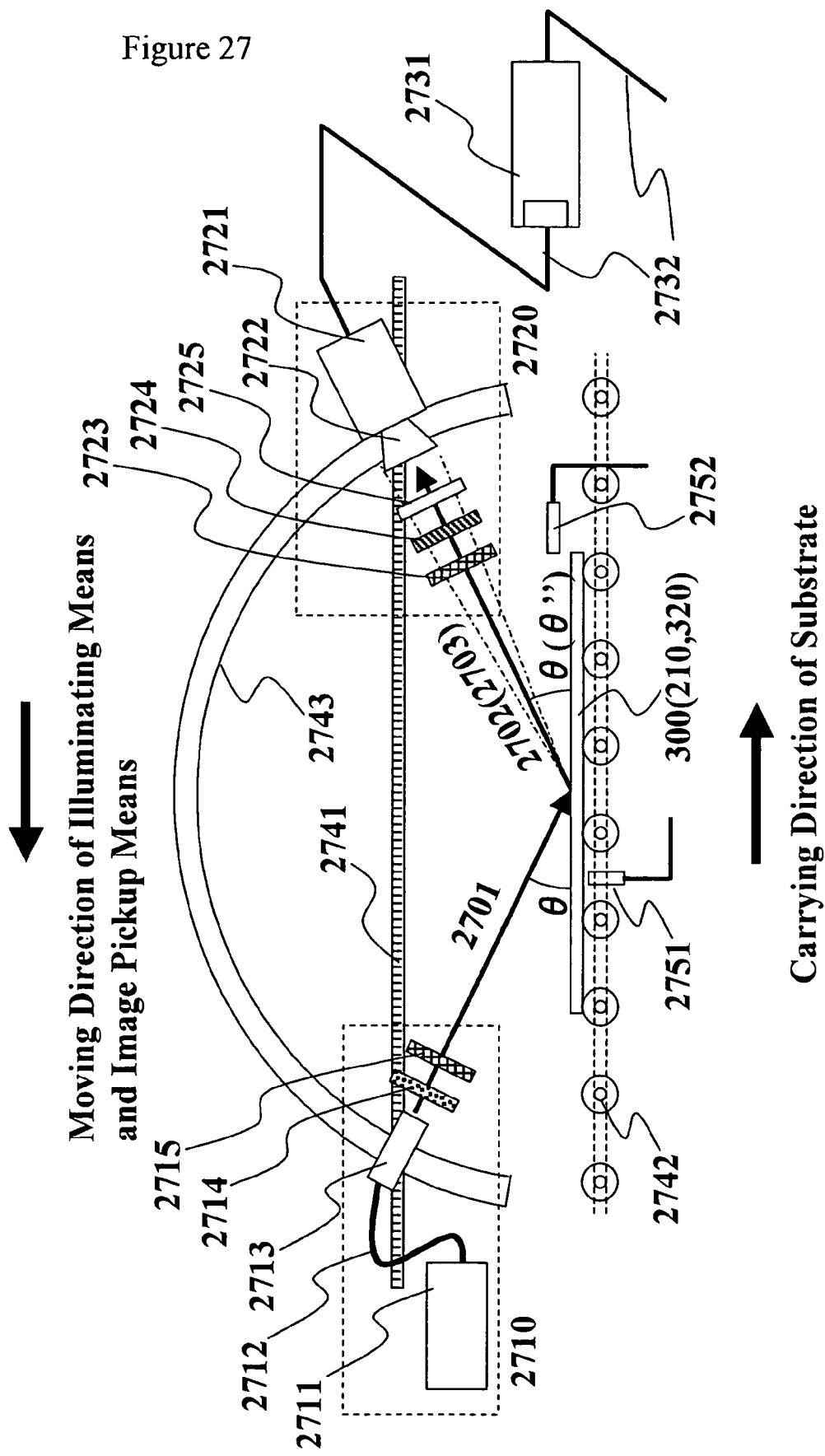
FIG. 27 is a schematic illustration of an inspection device for realizing the inspection method of the present invention.

FIG. 27 is a schematic illustration of the inspection device for realizing the inspection method of the present invention. The inspection device of the present invention basically comprises an illuminating means 2710 for allowing the incoming light 2701 to be incident on the surface of the phosphor with respect to the substrate 300 to be inspected (or substrates 310 and 320), an imaging means 2720 for capturing the reflected light 2702 or the fluorescent photogenesis 2703 from the liquid phosphor surface by a predetermined angular aperture, and a signal processing means 2731 for processing the intensity signal of the reflected light 2702 or the fluorescent photogenesis 2703 obtained by the imaging means, and the illuminating means 2710 and the imaging means 2720 are fixed by an angle adjusting mechanism 2743 capable of changing the angle of light incidence/reflection $\theta$ between 20° and 80° without changing the distance to the reflection point of the light. When the inspection method of the present invention is carried out in the phosphor inspection step (I) 252, the angle of light incidence/reflection θ preferably satisfies the formula 3 below, where H is the height of the partition walls constituting the groove, $H_p$ is the surface height of the phosphor, $L_\alpha$ is the width of the groove constituted of the partition walls with the phosphor applied thereto, and $L_\beta$ is the width of the groove constituted of the partition walls with the phosphor not applied thereto. In addition, when the inspection method of the present invention is carried out in the phosphor inspection step (II) 254, the angle of incidence θ of the light and the installation angle θ″ of the light receiving part 2721 need not be same.

$$\tan^{-1}\frac{2(H-H_p)}{L_\alpha} < \theta \le \tan^{-1}\frac{2H}{L_\beta}$$

In addition, the phosphor forming state for each groove over the whole length in the substrate moving direction can be inspected for the substrate 300 (or 310 and 320) by moving at least one of the illuminating means 2710 and the imaging means 2720, or the substrate 300 (or 310 and 320) to continuously picking up the image of the reflected light 2702 or the fluorescent photogenesis 2703 by the imaging means 2720.

In order to move the illuminating means 2710 and the imaging means 2720, a moving means 2741 such as a gantry stage is available, and in order to move the substrate 300 (or substrates 310 and 320), a substrate carrying means 2742 such as a stage or a roller carrier capable of loading, fixing and moving the substrate may be available. The intensity signal of the reflected light obtained by the imaging means 2720 is input in the signal processing means 2731 as image information through the signal transmitting means 2732, and the signal processing means 2731 processes the signal, measures the phosphor forming state, and further determines non-defective products or defective products.

In addition, description will be made in detail on the illuminating means 2710 and the imaging means 2720 of the inspection device of the present invention. Firstly, the illuminating means 2710 basically comprises a light source part 2711, a light ejection port 2713, and a light transmission part 2712 for connecting these components to each other. In particular, regarding an exiting port 2713, the size of the entire device need not be larger than required. In order to prevent wasteful diffusion of the quantity of light of a light source, the shape is slit-like, the width is 10 mm or under, and the longitudinal in the longitudinal direction is 1,000 mm or under, preferably. Further, the slit width is preferably at least 0.3 mm so that a measurement part can be illuminated with sufficient intensity because the inspection is carried out by using a standard light source on the market, and the slit length in the longitudinal direction is preferably at least 10 mm so that the measurement part can be illuminated in a sufficiently uniform manner in order to carry out the inspection with high accuracy.

The light source part 2711 of the illuminating means 2710 includes a halogen light source, a metal halide light source, a black light source, a high-voltage mercury lamp, a low-voltage mercury lamp, and an excimer lamp, a light transmission part 2712 includes optical fiber, an exiting port 2713 includes a light guide and a slit plate having an aperture in a material of low light transmittance ratio which are capable of disposing one side end of the optical fiber in the line and exiting the light in the line. If the light source part 2711 and the light ejection port 2713 cannot be separated from each other according to the kind of the light source, the light transmission part 2712 is not used, but the light ejection port 2713 may be installed directly on the light source part 2711.

In addition, either of or both of a light diffusing means 2714 for bringing the correlation between the surface shape and the brightness close to the proportional relationship by diffusing the exiting light and the light polarizing direction selecting means 2715 for selecting the light in the desired polarizing direction out of the exiting light in order to improve the image capture contrast by using only the light in the desired polarizing direction in the inspection may be fitted to the exiting port 2713. The light diffusing means 2714 includes a light diffusing sheet, and the light polarizing direction selecting means 2715 includes a polarizing plate.

Next, a light receiving part 2721 of an imaging means 2720 comprises light receiving elements disposed in a one-dimensional manner, and includes a CCD line sensor camera and a photomal. In addition, the light receiving part 2721 has a light converging part 2722 for focusing the image on the light receiving element, and the light converging part 2722 has an image capture angular aperture adjusting mechanism capable of adjusting the image capture angular aperture so as to satisfy the inequalities 4 below. A light converging part 2722 includes an optical lens, and the upper and lower limit values in the inequalities indicate the possible values realized in a stop mechanism of the optical lens for general purpose. In the inspection device of the present invention, the longitudinal direction of the light ejection port 2713 and the arranging direction of the light receiving elements of the light receiving part 2721 are same as the longitudinal direction of the phosphor formed on the substrate.

$$1.2 \le F \le 2.0$$

In addition, a light polarizing direction selecting means 2723 for selecting the light in the desired polarizing direction out of the reflected light may be fitted to the light receiving part 2721 in order to improve the image capture contrast by using only the light in the desired polarizing direction in the inspection. The light polarizing direction selecting means 2725 includes a polarizing plate. In addition, a received light intensity attenuating means 2724 for attenuating the intensity of the light-incident on the light receiving part 2721 so as to satisfy the inequalities 5 may be fitted to the light receiving part 2721. The received light intensity attenuating means 2724 may include an extinction filter, and the upper and lower values in the inequalities 5 are set so as to carry out the inspection with high accuracy when the image capture angular aperture is in a range of the above inequalities 4.

$$0.3 \le OD \le 2.0$$

A captured image wavelength selecting means 2725 for selecting the wavelength of the light to be captured may be fitted to the light receiving part 2721. The captured image wavelength selecting means 2725 includes optical filters such as a color glass filter and a vapor deposition filter. When the above light receiving part 2721 has already an image capture wavelength selecting mechanism, the image capture wavelength selecting means 2725 need not be provided. The light receiving part 2721 having the image capture wavelength selecting mechanism may include a three-plate type CCD color line sensor camera.

When inspecting the phosphor forming state by the inspection method of the present invention, if the resolution in the direction orthogonal to the arranging direction of the light receiving element of the imaging means is too large for the width of the phosphor which is the object to be inspected, sufficient brightness information cannot be obtained for the inspection. On the other hand, if the resolution is too small, brightness information obtained in the inspection of one substrate is too much, and the signal processing is burdened. Thus, at least one of the scan rate of the imaging means and the speed of relative movement 300 (or 310 or 320) with respect to the illuminating means 2710 and the imaging means 2720 is preferably adjusted so as to satisfy the following inequalities 1, where R is the resolution of the imaging means, and $L_\alpha$ is the width of the groove which is formed of the partition walls and coated by the phosphor.

$$3 \le \frac{L_\alpha}{R} \le 10$$

In addition, a substrate advancement sensing means 2751 for automatically sensing the advancement of the substrate and starting the image capture at good timing may be fitted to the inspection device of the present invention. The substrate advancement sensing means 2751 may include a photoelectric sensor.

Still further, a substrate moving speed measuring means 2752 for measuring the substrate carrying speed and improving the accuracy of the inspection may be fitted to the inspection device of the present invention. The substrate moving speed measuring means 2752 may include a contact type speed indicator and a laser Doppler type speed indicator.

Next, description will be made on a manufacturing method of a display panel using the inspection method of the present invention with the back plate of the PDP as an example.

In the manufacturing method of the present invention, at least one of inspection steps of inspecting the forming state of liquid phosphor or the fluorescent layer by using the inspection method immediately after a step 251 of applying liquid phosphor between the partition walls, or immediately after a step 253 for drying liquid phosphor and forming the fluorescent layer.

The object to be inspected by the inspection method of the present invention is not continuously manufactured like plastic film, but separately manufactured for each individual like the back plate of the PDP. Thus, to keep the consistent inspection sensitivity for each individual is to ensure the quality of every product with high accuracy by the inspection method of the present invention. Here, the element most important for keeping the consistent inspection sensitivity for each individual is the quantity of light for the inspection. For example, if the substrate is inspected by the light of 50% the quantity of the light used in the inspection of the substrate immediately before the previous substrates, for example, within the manufacture lot, brightness information obtained by the imaging means is also about 50% of brightness information on the inspection obtained immediately before the previous inspection. Thus, degradation of the inspection sensitivity is a clear fact.

One of the causes for different intensity of the inspection light by the substrate inspection includes degradation of the illuminating means. Further, since the reflection characteristic of the inspection light is different according to the individual difference, lot number, kinds, etc. of the substrate to be inspected, brightness information obtained by the imaging means is different. In order to solve this problem and obtain the consistent inspection sensitivity in every substrate to be inspected, the quantity of light of the inspection light emitted by the illuminating means must be controlled.

Figure 28:
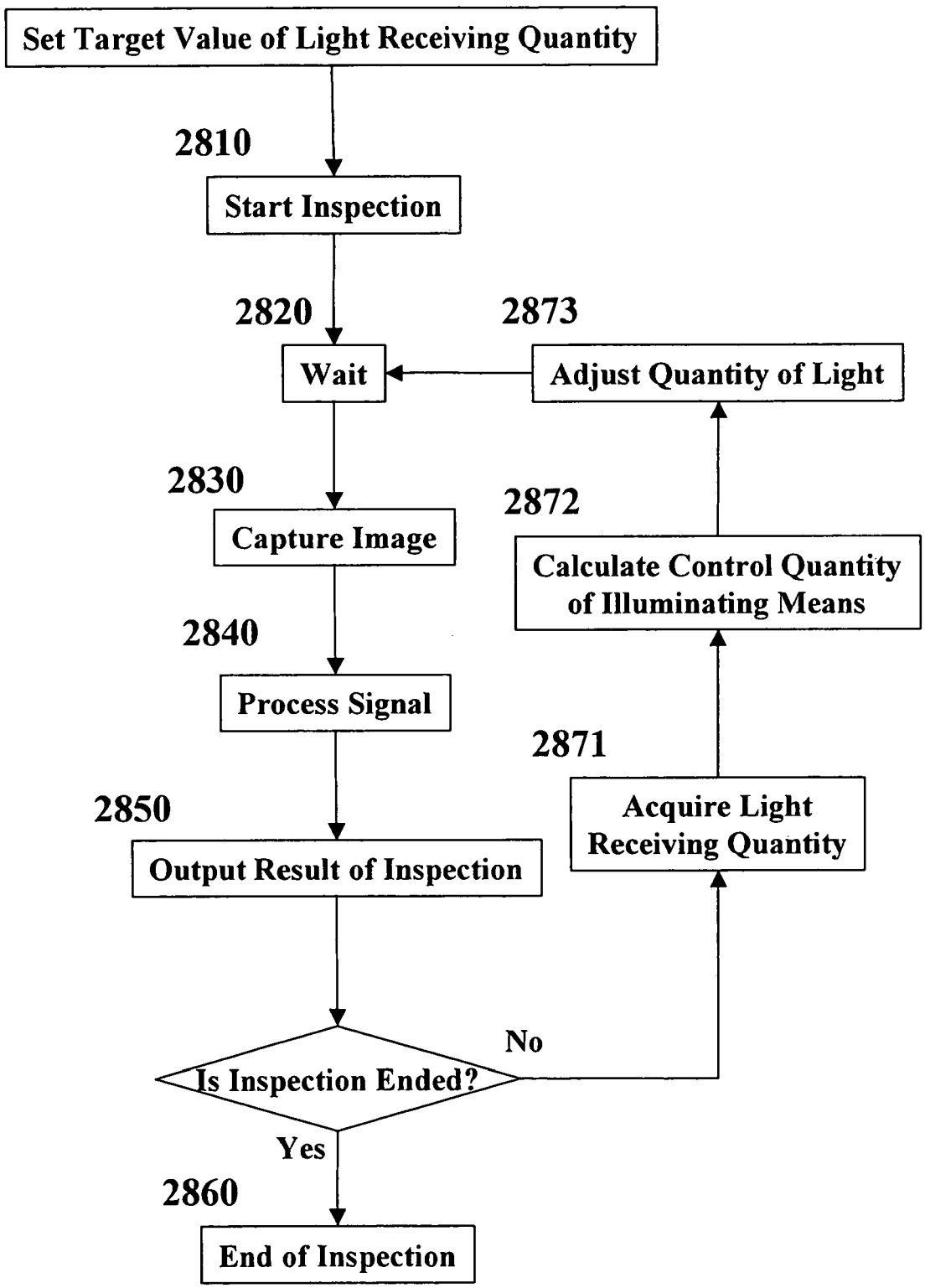
FIG. 28 is a flowchart showing an example of correction for the quantity of light.

Quantity-of-light correction of the inspection light will be described with reference to FIG. 28. FIG. 28 is a flowchart for showing the inspection method of the present invention and an example of a quantity-of-light correcting method of the inspection light. To perform the quantity-of-light correction, the target light receiving quantity which is the target for quantity-of-light correction is registered in the inspection device (2820) in advance before starting the inspection (2810). After starting the inspection (2810), image of the substrate to be inspected is captured through the waiting state (2820) after starting the inspection (2810). The obtained image signal is processed (2840), and acceptance or rejection of the substrate to be inspected is determined (2850). In addition, when processing the signal, information on the light receiving quantity obtained in the inspection of the substrate is acquired (2871), the control quantity of the illuminating means is calculated so as to obtain the quantity of light closer to the target light receiving quantity which is firstly set in the inspection of the next substrate (2872), and the illuminating means is controlled (2873). The constantly consistent inspection sensitivity can be obtained by this quantity-of-light correcting method irrespective of degradation of the illuminating means, individual difference of the substrates to be inspected, lot number, and kind.

Further, one of the large characteristics of the inspection method of the present invention is that any groove and/or part with abnormality in the phosphor forming state generated therein can be identified. When any abnormality occurs in the phosphor forming state, the cause of generation lies in the step 251 of applying liquid phosphor to the grooves. In this step 251, three kinds of means for applying liquid phosphor are well known as described above, and when any defective application of liquid phosphor occurs, the cause for defective application lies in the position of generating defective application and a part corresponding thereto in each kind of means. If the groove and part at which the abnormality in the phosphor forming state occurs can be identified, it is understood that the cause for generating the defective application is present in the liquid phosphor applying means and the part corresponding thereto, and the cause for the defective application can be eliminated immediately.

This means that, if the cause for generating the defective application cannot be identified in the liquid phosphor applying means, the treatment for eliminating the cause for defective application must be taken for all liquid phosphor application means, and in the manufacturing method of the present invention, the place in which the cause for generating the defective application is present can be identified, and the treatment for eliminating the defective application may be taken to the identified part of the liquid phosphor applying means. The treatment for eliminating the cause for defective application includes the rapid change of a nozzle, and elimination of nozzle stuffing by an ultrasonic cleaning machine if, for example, the liquid phosphor applying means is a nozzle applying method.

In addition, in the manufacturing method of the present invention, the groove and part at which any abnormality in the phosphor forming state in the defective substrate are identified, and the defective substrate is repaired, and reconditioned as a non-defective product.

Figure 29:
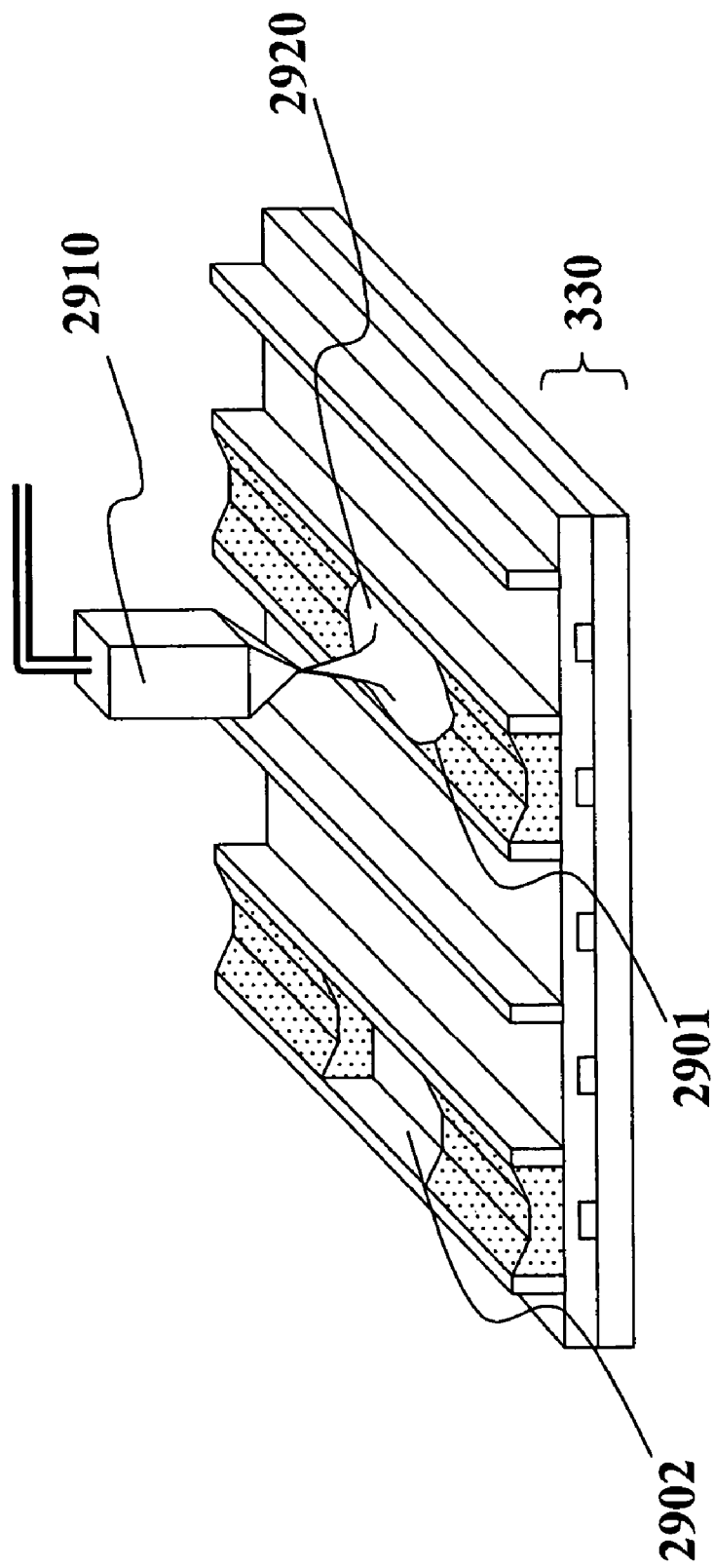
FIG. 29 is a schematic illustration indicating a step of correcting defects in liquid phosphor in a manufacturing method of the present invention.

Description will be made on a defect repairing method when any defective substrate is discovered in the phosphor inspection step (I) 252 with reference to FIG. 29. When the inspection device of the present invention detects any defects, the substrate 330 with liquid phosphor of the first color including the defective parts 2901 and 2902 is carried to the defect repairing step (I) 261 before performing the step 253 of drying liquid phosphor to form a fluorescent layer. In the defect repairing step (I) 261, defect position information of the substrate 330 is obtained from the inspection device, the defect repairing nozzle 2910 is moved to the position of the defect 2901, and the liquid phosphor 2920 is applied to the defective position. This operation is repeated until all defects present in the substrate 330 are repaired, and when all defects are repaired, the substrate 330 is carried out to the step 253 of drying liquid phosphor to form the fluorescent layer.

Figure 30:
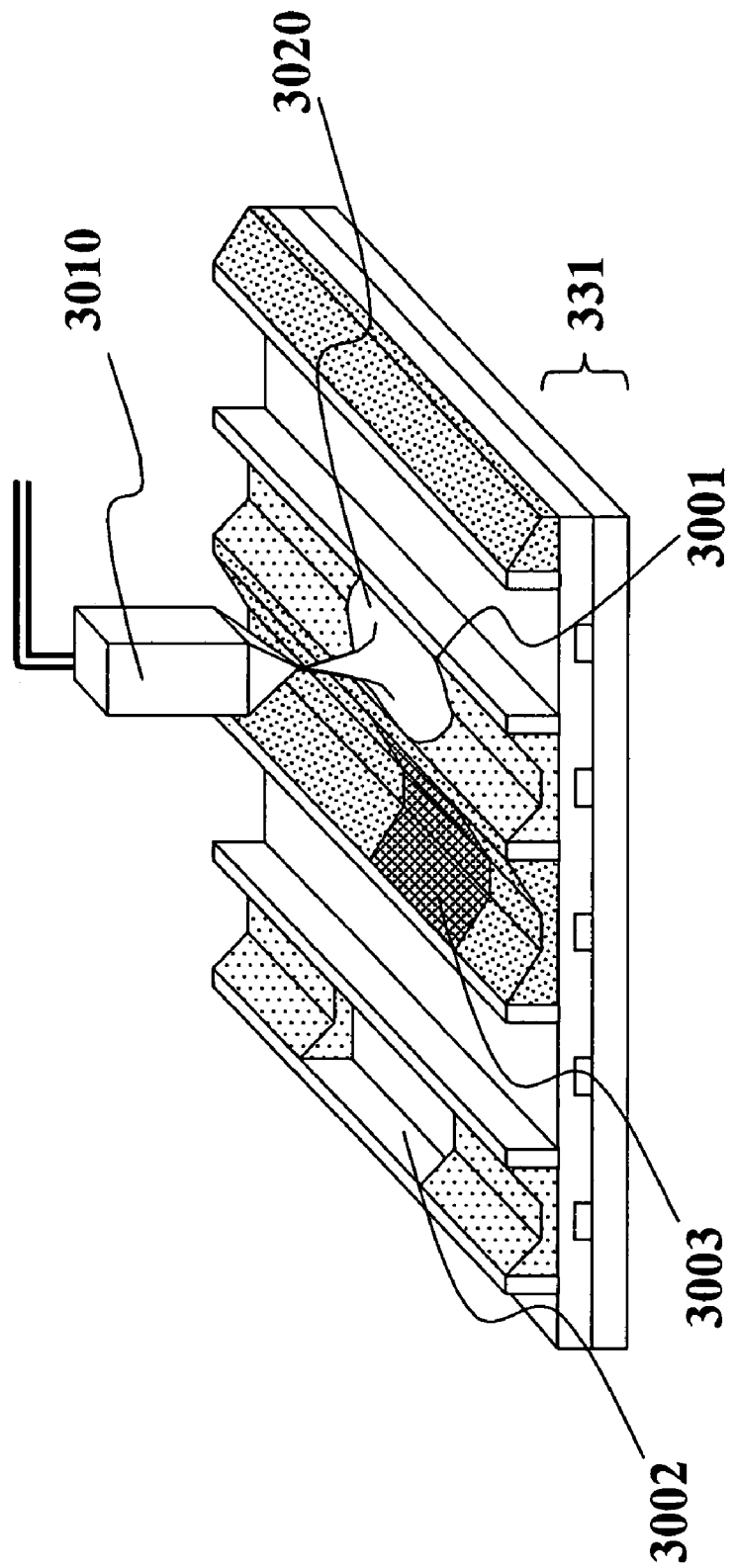
FIG. 30 is a schematic illustration indicating a step of correcting defects in the fluorescent layer in a manufacturing method of the present invention.

Description will be made on the defect repairing method when any defective substrate is discovered in the phosphor inspection step (II) 254 with reference to FIG. 30. When the inspection device of the present invention detects any defect, the substrate 331 including defective parts 3001 and 3002 with the phosphor up to the second color coated thereon is carried in the defect repairing step (II) 262. In the defect repairing step (II) 262, information on the defect position of the substrate 331 is obtained from the inspection device, the defect repairing nozzle 3010 is moved to the position of the defect 3001, and the liquid phosphor 3020 is applied to the defect position. This operation is repeated until all defects present in the substrate 331 are repaired, and when all defects are repaired, the substrate 331 is carried out to the step 253 of drying liquid phosphor to form the fluorescent layer. If phosphor for coating is still left, it may be carried out to the step 251 of applying liquid phosphor between the partition walls.

As described above, the object of the present invention is to provide a manufacturing method in which the phosphor forming state is inspected with high accuracy by using the inspection method of the present invention, troubles in the steps are rapidly repaired if defects are continuously generated, the yield is improved with degrading the yield rate by repairing defective substrates and reconditioning them to non-defective products, and the substrate of high quality and high reliability is manufactured.

EMBODIMENT

Details of the present invention will be described using several embodiments.

In the first embodiment of the present invention, a back plate of the PDP was manufactured by performing only the phosphor inspection step (I) without performing the phosphor inspection step (II) in the step shown in FIG. 2. A substrate having the grooves of the width L shown in FIGS. 3, 6 and 15 was used for the objective substrate to be manufactured. A nozzle applying method was used in the step 251 of applying liquid phosphor to the grooves, and the inspection device shown in FIG. 27 was used in the phosphor inspection step (I).

In particular, the inspection device of the liquid phosphor forming state will be described below in detail. A halogen light source was used for the light source part 2711 of the illuminating means 2710, the light is led to the light ejection port of the width of 0.5 mm×the length of 100 mm through optical fibers, a diffusion plate and a polarizing plate are provided on the light ejection port, the CCD line sensor camera with the light receiving elements of 2042 pixels arrayed in the light receiving part 2721 of the imaging means 2720 in a one-directional manner was used, a general purpose collective lens was used for the light converging part 2722, and the F number was determined to be set to 1.2 by a stop mechanism of the collective lens regarding the image capture angular aperture θk.

Further, by maximizing the stop of the collective lens, the light of the intensity not lower than the capacity of the light receiving element of the imaging means is incident, and thus, the received light intensity attenuating means 2724 is installed before the collective lens to attenuate the intensity of the incoming light. A general purpose extinction filter of OD=0.6 was used for the received light intensity attenuating means 2724.

In addition, regarding the angle of light incidence/reflection θ of the incoming light 2701 and the reflected light 2702 used in the inspection, the optimum angle of light incidence/reflection θ for the inspection was calculated from the back plate design value and the image capture angular aperture θk, and the value was reflected therein. A general purpose image processor was used for the signal processing means 2731 to process brightness information obtained by the imaging means 2720. The detailed processing content includes the measurement of the application volume of liquid phosphor applied to the grooves with all liquid phosphor applied thereto from the brightness peak waveform obtained from the CCD line sensor camera, the setting first and second thresholds appropriate for the brightness peak waveform, and the inspection that the liquid phosphor application state of the grooves indicated by the brightness peak below the first threshold or the brightness peak above the second threshold is defective. Further, in order to carry out the inspection over the entire substrate, the substrate 300 was moved, and a roller carrier was used for the substrate carrying means 2742.

In addition, regarding the resolution in the substrate carrying direction of the imaging means, the camera scan rate was adjusted so that the sufficient inspection accuracy is maintained, and brightness information not to impose a burden on the signal processing means can be obtained.

In order to prevent degradation of the inspection accuracy attributable to the change in the substrate carrying speed, a method was employed, in which the substrate carrying speed is calculated from the brightness peak interval of the brightness signal obtained in the inspection by the waveform signal processing means 2731, and acceptance or rejection of the substrate 300 to be inspected is determined with reference to the obtained result.

In order to inspect a plurality of substrates at the consistent sensitivity, a method was employed, in which the quantity-of-light value is calculated from image information obtained for each inspection of one substrate, the control quantity of the illuminating means is calculated based thereon, and the quantity of light is corrected.

In addition, when a defect occurs, the cause for the defect is rapidly identified, the step is repaired, the defective substrate is subjected to the defect repairing step (I) to repair the defect and reconditioned to a non-defective substrate.

As a result, the inspection was carried out at the angle of light incidence/reflection θ which is calculated from the back plate design value and the image capture angular aperture θk by the above formula and optimum for the inspection, and high S/N ratio was obtained, leading to easy classification of the grooves to be inspected from the grooves which need not be inspected. Liquid phosphor was applied so that the surface shape is concave. The correlation between the surface shape and the brightness is substantially proportional by diffusing the incoming light, and increasing the image capture angular aperture of the camera, and the inspection sensitivity could be improved even under the condition of small application volume.

In the step of applying liquid phosphor to the grooves of the substrate 300, coagulate of the composition of liquid phosphor was stuffed in one hole of the nozzle for applying liquid phosphor and defective application of liquid phosphor occurred, and this was detected by the above inspecting means. Further, by identifying the position of the defective part, the nozzle need not be detached from an applicator for overhaul cleaning, and the stuffed hole of the nozzle was ultrasonic-cleaned while the nozzle being fitted to the applicator, and the stuffed coagulate was removed, and occurrence of continuous defects could be avoided in the minimum defect occurrence frequency and in the minimum recovering work. The defective substrate was subjected to the defect repairing step (I), and reconditioned as a non-defective substrate.

In addition, in the step of applying liquid phosphor to the grooves of the substrate 300, an abnormality occurred in the set value of a pressurizing device of the nozzle applicator for applying liquid phosphor, and defective application occurred in that liquid phosphor of the amount more than the specified value was applied, and this was detected by the above inspecting means. Occurrence of continuous defects could be avoided in a minimum defect occurrence frequency and in a minimum recovering work by identifying the position of defective parts and the application volume to estimate the appropriate set value of the pressurizing device, and reflecting the estimation to the device. The defective substrate was subjected to the defect repairing step (I), and reconditioned as a non-defective substrate.

Variance in the substrate feeding speed of about ±50% caused by the eccentricity of a motor shaft of the roller carrying machine occurred during the inspection for a plurality of sets of liquid phosphor, but the inspection could be carried out with high accuracy without mistakenly detecting normal liquid phosphor as defects.

In the inspection carried out for a plurality of substrates during the operation in the manufacturing step, the variance of the quantity-of-light value obtained by the imaging means was about ±5%, and the inspection could be carried out for the plurality of substrates at substantially consistent sensitivity.

The substrate to be manufactured was changed to the substrate of different groove width by RGB like the substrate 310 shown in FIG. 4. Similar to the above, the inspection was carried out at the angle of light incidence/reflection θ calculated from the back plate design value and the image capture angular aperture θk and optimum for the inspection, and high S/N ratio was obtained, leading to easy classification of the grooves to be inspected from the grooves which need not be inspected. Similar to the above, defective application of liquid phosphor occurred, and was detected to remove the cause for the defects, and the defective substrate was reconditioned to a non-defective substrate.

Figure 22:
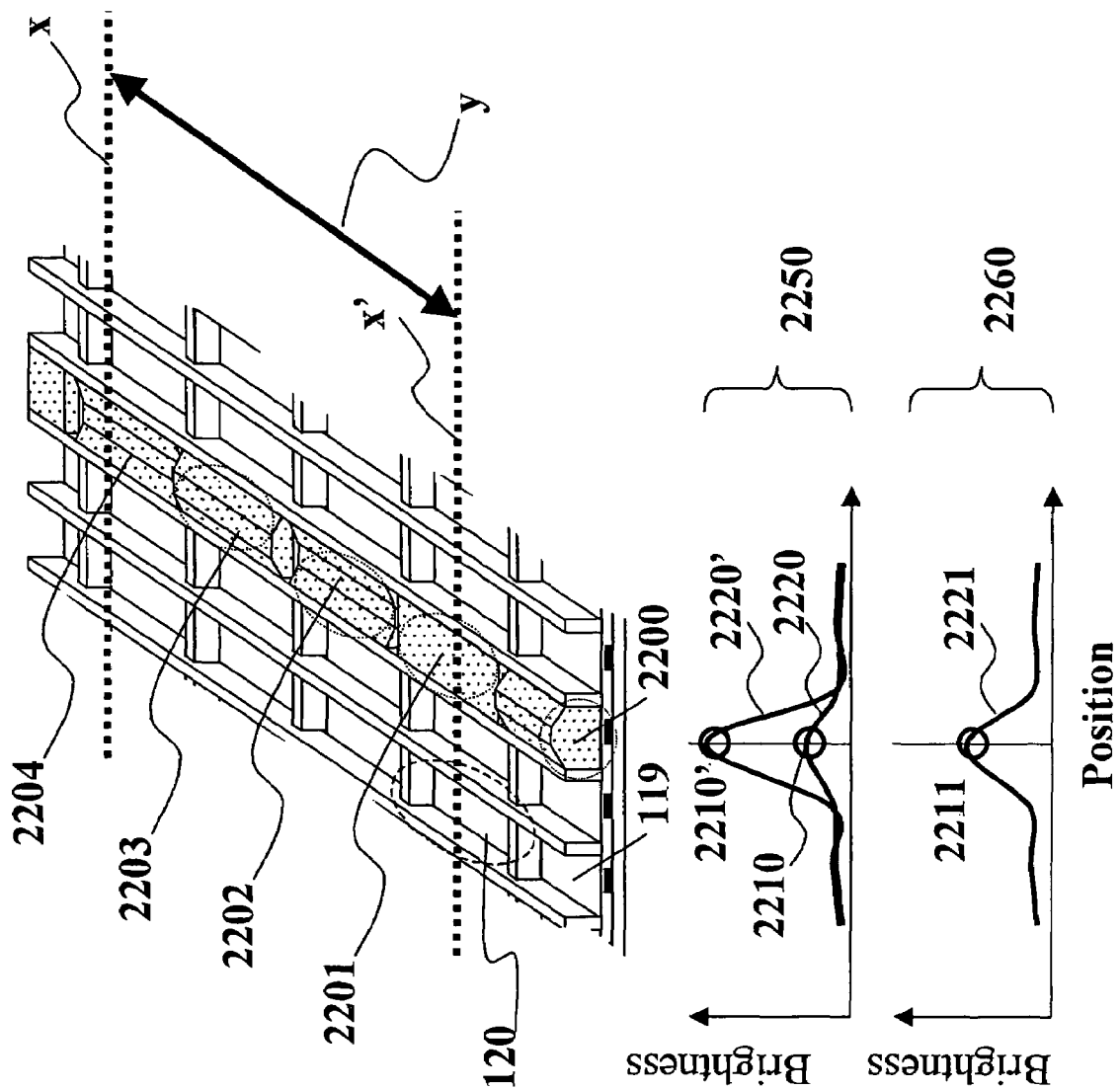
FIG. 22 is a schematic illustration of liquid phosphor applied to a substrate having grooves with transverse ribs, and brightness signal waveform obtained by an inspection direction of the present invention.

Next, for the second embodiment of the present invention, the substrate 320 having the groove with transverse ribs shown in FIGS. 5 and 22 was manufactured by the manufacturing method according to the first embodiment. In this case, a black light for irradiating the light of the wavelength of mainly 360 nm was used for the light source part 2711 of the illuminating means 2710, and a slit plate was used for the light ejection port 2713, respectively, and the light transmission part 2712 was removed. In addition, a laser Doppler type speed indicator was installed for the substrate moving speed measuring means 2752.

Further, in this case, in order to improve the inspection accuracy, a method for determining acceptance or rejection of the substrate was employed, in which the signal processing means integrates brightness data for a plurality of light receiving elements to obtain the average brightness waveform.

As a result, the liquid phosphor application volume for the substrate 320 was different for each cell held by transverse ribs, and it was confirmed that defective parts can be detected with high accuracy by averaging brightness information for 200 pixels of the light receiving elements of the camera. It is also confirmed that the S/N ratio is higher than that by the inspection method according to the first embodiment by using the light of the wavelength of 360 nm in the inspection.

Here, in the step of applying liquid phosphor to the grooves of the substrate 320, twenty holes of the nozzle for applying liquid phosphor were simultaneously stuffed by impurities contained in liquid phosphor before application, and defective application of liquid phosphor occurred, and this was detected by the above inspection method. In this case, it was determined that change of the nozzle led to earlier restoration of the step than cleaning all holes, and the nozzle could be changed. Further, the step could be stabilized by changing liquid phosphor containing much impurities with that of another lot. In addition, the defective substrate was subjected to the defect repairing step (I), and reconditioned as a non-defective substrate.

Variance in the substrate feeding speed of about ±50% caused by the eccentricity of a motor shaft of the roller carrying machine occurred during the inspection for a plurality of sets of liquid phosphor, but the inspection could be carried out with high accuracy without mistakenly detecting normal liquid phosphor as defects with reference to the substrate carrying speed information from the laser Doppler speed indicator.

Next, as the third embodiment of the present invention, liquid phosphor was applied in the first manufacturing method so that the surface height of liquid phosphor is 85% of the height of the partition walls constituting the groove.

As a result, it was confirmed that the intensity of the reflected light S incident on the camera from the surface of liquid phosphor as an object to be inspected was considerably increased, and the S/N ratio was higher on the whole than that by the inspection method of the first embodiment.

Next, as the fourth embodiment of the present invention, the substrate of different width for RGB like the substrate 310 shown in FIG. 4 was manufactured in the first manufacturing method. Liquid phosphor was applied successively from the color of liquid phosphor to be applied to the widest groove, ending by the color of liquid phosphor applied to the narrowest groove.

As a result, in the inspection of liquid phosphor applied to the narrowest groove, it was confirmed that the reflected light N reflected from the widest groove and incident on the camera was considerably reduced in quantity, and the S/N ratio was higher on the whole than that by the inspection method of the first embodiment.

Next, as the fifth embodiment of the present invention, the grooves which need not be inspected in the first manufacturing method were covered, and a chromium mask designed so that an aperture is opened only for the groove to be inspected was installed on the substrate to be inspected.

As a result, it was confirmed that the reflected light N reflected from the groove which need not be inspected and incident on the camera was considerably reduced in quantity, and the S/N ratio was higher on the whole than that by the inspection method of the first embodiment.

Next, as the sixth embodiment of the present invention, the phosphor inspection step (I) was not performed in the step shown in FIG. 2, but only the phosphor inspection step (II) was performed to manufacture the back plate of the PDP. The substrate having the grooves of the same width L shown in FIGS. 3 and 7 was used for the substrate to be manufactured. The nozzle applying method was used in the step 251 of applying liquid phosphor to the grooves, and the inspection device shown in FIG. 27 was used in the phosphor inspection step (II).

Description will be made below in detail on the inspection device of, in particular, the fluorescent layer applying state.

An excimer lamp was used for the light source part 2711 of the illuminating means 2710, and the light ejection port 2713 and the light transmission part 2712 were detached. The light receiving elements 2042 pixels were arrayed in a one-dimensional manner on the light receiving part 2721 of the imaging means 2720, a three-plate type color CCD line sensor camera capable of respectively selecting RGB lights and picking up the image was used, and a collective lens on the market was used for the light converging part 2722.

In addition, the angle of incidence θ of the incoming light 2701 used in the inspection was set to be 80°, and the angle of installation θ" of the imaging means for capturing the light was set to be 30°. A general purpose image processor was used for the signal processing means 2731 for processing brightness information obtained by the imaging means 2720. The content of the signal processing and the substrate moving method are similar to those in the first embodiment of the present invention.

In addition, in order to inspect the fluorescent layer over the entire surface of the substrate to be inspected, six cameras were disposed continuously in the same direction as the grooves on the substrate, and image information obtained from each camera was processed by each exclusive image processor.

As a result, it was confirmed that the phosphor forming state can be inspected with high accuracy in the range of the whole amount of phosphor without being influenced by the condition of the fluorescent layer application volume in manufacturing the substrate.

Here, in the step of applying liquid phosphor to the grooves of the substrate 300, bubbles contained in liquid phosphor before application were discharged from one hole of the nozzle for applying liquid phosphor, and the defect of non-application of about 10 mm in the same direction as that of the grooves occurred in the phosphor, and this was detected by the inspecting means. Remaining bubbles were forcibly discharged from the nozzle with the nozzle fitted to the applicator, the subsequent steps could be stabilized with a minimum restoring work, and the defective substrate was subjected to the defect repairing step (II) and reconditioned as a non-defective substrate.

As a matter of course, in order to control the quality of the products with higher accuracy, both the phosphor inspection step (I) and the phosphor inspection step (II) may be performed in the manufacturing method of the present invention.

From the above results, it is confirmed that the present invention contributes much to the improvement of the yield in manufacturing the back plate of the PDP.

As described above, it is demonstrated that, in the manufacture of, in particular, the back plate of the PDP, the inspection method and the inspection device, and the manufacturing method of the present invention are effective, and these are also effective in the manufacture of products with a pattern formed on the substrate represented by, for example, an LCD color filter and a semi conductor substrate.

INDUSTRIAL APPLICABILITY

According to the inspection method, the manufacturing method and the manufacturing device of the present invention, in the manufacturing step of a spread display panel such as the back plate of the PDP, the yield can be improved without degrading the yield rate, and the substrate of high quality and high reliability can be manufactured by inspecting the forming state of a plurality of sets of phosphor formed in the predetermined grooves with high accuracy, rapidly repairing troubles of the step when continuous defects occur, repairing the defective substrate, and reconditioning the defective substrate into a non-defective substrate.

The invention claimed is:

1. A method of inspecting a display panel comprising a substrate, a plurality of spaced apart, parallel partition walls provided on the substrate and fluorescent layers formed by applying a phosphor in each groove formed between the partition walls, with a combination of an illuminator and an imaging device, the method comprising the steps of:
   moving relatively the substrate and the combination of illuminator and imaging device in a direction across the grooves;
   illuminating the grooves in sequence with light emitted from the illuminator and receiving a light emitted, based on the illuminating, from the grooves in sequence by the imaging device, during movement of the substrate or the combination of illuminator and imaging device;
   measuring bright and dark signals of the light received by the imaging device; and
   measuring volume of the phosphor applied in the grooves based on the obtained signals,
   wherein an ejection port of the illuminating device for emitting light is formed with a slit, and
   wherein the width of the slit is in the range of 0.3 mm to 10 mm, and the length of the slit is in the range of 10 mm to 1000 mm.

2. The method according to claim 1, wherein a roller is used to move the substrate or the combination of the illuminator and the imaging device.

3. The method according to claim 1, further comprising measuring a relative speed between the substrate and the combination of the illuminator and the imaging device with a moving speed measuring device.

4. The method according to claim 3, wherein the signals obtained by the measuring thereof are corrected by the relative speed obtained by the moving speed measuring device, and the volume of the phosphor applied in the grooves is measured by the corrected signals.

5. The method according to claim 3, wherein the moving speed measuring device calculates the relative speed based on the interval of the partition walls obtained by the imaging means.

6. The method according to claim 1, wherein the illuminator irradiates ultraviolet rays having a wavelength of 260 nm or less on the fluorescent layers, and fluorescence photogenesis from the fluorescent layers forms the bright and dark signals and is captured by the imaging device.

7. The method according to claim 1, wherein the fluorescent layers are liquid.

8. The method according to claim 1, wherein the imaging device mainly captures light reflected from the fluorescent layer with an angle being substantially the same as the incident angle of an incident light emitted from the illuminator to the fluorescent layer, among lights reflected from the fluorescent layer.

9. The method according to claim 1, wherein the illuminator has a light diffuser that diffuses light emitted from the illuminator.

10. The method according to claim 1, wherein the illuminator has a light polarizing direction selector that selects a light having a desired polarized light direction among lights emitted from the illuminator.

11. The method according to claim 1, wherein the imaging device has a plurality of light receiving elements.

12. The method according to claim 11, wherein the plurality of light receiving elements are arranged in a line.

13. The method according to claim 11, wherein a signal processor adds signals of a plurality of light receiving elements of the imaging device and averages them, obtains a signal peak for each of the fluorescent layers from averaged signal waveforms, obtains a signal peak waveform for each of the fluorescent layers by linking the signal peaks, and measures volume of the phosphor applied in each of the grooves from the signal peak waveform.

14. The method according to claim 1, wherein the imaging device has a light polarizing direction selector that selects a light having a desired polarized light direction from the lights reflected from the fluorescent layer.

15. The method according to claim 1, further comprising a signal processor which calculates intensity of inspection light incident on the fluorescent layer from the illuminator based on the signals obtained by the imaging device, and corrects the illuminator so that the intensity of the inspection light in an inspection of a following display panel becomes a preset target value with reference to the obtained intensity of the inspection light.

16. A method of inspecting a display panel comprising a substrates, a plurality of spaced apart, parallel partition walls provided on the substrate and fluorescent layers formed by applying a phosphor in grooves formed between the partition walls, by using a combination of an illuminator and an imaging device, the method comprising the steps of:
moving relatively the substrate and the combination of illuminator and imaging device in a direction across the grooves;
illuminating the grooves in sequence with light emitted from the illuminator and receiving a light emitted, based on the illuminating, from the grooves in sequence by the imaging device, during movement of the substrate or the combination of the illuminator and the imaging device;
measuring bright and dark signals of the light received by the imaging device; and
measuring volume of the phosphor applied in each of the grooves based on the obtained signal,
wherein the illuminator irradiates ultraviolet rays having the wavelength of 360 nm or less to the fluorescent layers, and the imaging device mainly captures ultraviolet rays having the wavelength of 360 nm or less emitted from the fluorescent layers.

17. A method of inspecting a display panel comprising a substrates, a plurality of spaced apart, parallel partition walls provided on the substrate and fluorescent layers formed by applying a phosphor in grooves formed between the partition walls in which the grooves have a width of $L_\alpha$, by using a combination of an illuminator and an imaging device in which the imaging device has a resolution of R, the method comprising the steps of:
moving relatively the substrate and the combination of the illuminator and the imaging device in a direction across the grooves;
illuminating the grooves in sequence with light emitted from the illuminator and receiving light emitted, based on the illuminating, from the grooves in sequence by the imaging device, during movement of the substrate or the combination of the illuminator and the imaging device;
measuring bright and dark signals of the light received by the imaging device; and
measuring volume of the phosphor applied in each of the grooves based on the obtained signals,
wherein the width of $L_\alpha$ of the groove and the resolution of R of the imaging device satisfy the following equation (1):

$$3 \leq \frac{L_\alpha}{R} \leq 10 \quad (1)$$

18. A method of inspecting a display panel having a substrate and a plurality of fluorescent layers formed in a plurality of grooves formed by partition walls on the substrate comprising capturing at least reflected light at an angle of incidence θ out of light incident on surfaces of the fluorescent layers at the angle of incidence θ such that the angle of incidence θ forms an angle at which the reflected light at the angle of reflection θ obtained by allowing the light to be incident on a groove bottom partition without any phosphor applied thereto at the angle of incidence θ is blocked by the partition walls.

19. The method according to claim 18, wherein equation (2) is satisfied as follows:

$$\tan^{-1}\frac{2(H-H_p)}{L_\alpha} < \theta \leq \tan^{-1}\frac{2H}{L_\beta}, \quad (2)$$

wherein H is the height of the partition walls forming the groove, $H_p$ is the surface height of phosphor, $L_\alpha$ is the width of the groove formed of the partition walls with phosphor applied thereto, θ is the angle of incidence and $L_\beta$ is the width of the groove formed of the partition walls without any phosphor applied thereto.

20. A device for inspecting display panels formed from a substrate and a plurality of fluorescent layers formed in grooves formed by partition walls comprising:
an illuminating means; and
an imaging means,
wherein the illuminating means and the imaging means are located to irradiate light and receive an image of the light at an angle of light incidence/reflection θ at which reflected light from a groove bottom portion without any phosphor applied thereto is blocked by the partition walls.

21. The device according to claim 20, wherein the imaging device has a lens passing through the reflected light and a F-number of F of the lens satisfies the following equation (4):

$$1.2 \leq F \leq 2.0 \quad (4).$$

22. The device according to claim 20, wherein the imaging device has a received light intensity attenuator and an optical damping intensity of OD in the visible light area of the received light intensity attenuator satisfies the following equation (5):

$$0.3 \leq OD \leq 2.0 \quad (5).$$

23. The device according to claim 20, wherein a mask having an aperture only in a part with phosphor to be inspected present therein is installed on an inspection surface of the substrate.

24. A display panel manufacturing method comprising the steps of:
preparing a substrate on which a plurality of spaced apart, parallel partition walls having a height of H are provided;
applying a phosphor in grooves formed between the partition walls to form a fluorescent layers having a surface height of $H_p$ in each of the grooves;
inspecting volume of the phosphor applied in each of the grooves; and drying the phosphor, wherein the height of H and the surface height of $H_p$ satisfy the following equation (6):

$$0.6 \leq H_p/H \leq 0.9 \qquad (6).$$

25. The method according to claim 24, wherein the grooves have at least two kinds of groove width and at least two kinds of the phosphors are prepared, and wherein the phosphor is applied successively from the groove having a widest groove width in the grooves and the grooves having the same groove width are applied with the same kind of the phosphor.

26. The method according to claim 24, wherein the inspecting step comprises the steps of:

preparing a combination of an illuminator and an imaging device;

moving relatively the substrate and the combination of the illuminator and the imaging device in a direction across the grooves;

illuminating the grooves in sequence with light emitted from the illuminator and receiving light emitted, based on the illuminating, from the grooves in sequence by the imaging device, during movement of the substrate or the combination of the illuminator and the imagine device;

measuring bright and dark signals of the light received by the imagine device; and measuring volume of the phosphor applied in the grooves based on the obtained signals by the measuring thereof, and inspecting a part in which the fluorescent layer emits the light after the substrate is built in a panel.

27. The method according to claim 24, wherein a fluorescent layer repairing device is provided, and the fluorescent layers are repaired based on results obtained by the inspecting step.

28. The method according to claim 24, wherein, when a defects in the volume of the phosphor is detected by the inspecting step, the applying step is stopped and the defect is repaired.

* * * * *

UNITED STATES PATENT AND TRADEMARK OFFICE
CERTIFICATE OF CORRECTION

| | |
|---|---|
| PATENT NO. | : 7,412,088 B2 |
| APPLICATION NO. | : 10/469618 |
| DATED | : August 12, 2008 |
| INVENTOR(S) | : Kuramata |

It is certified that error appears in the above-identified patent and that said Letters Patent is hereby corrected as shown below:

<u>In Column 7</u>

At line 3, please change "L" to -- L2 --; and at line 4, please change "L" to -- L3 --.

Signed and Sealed this

Fifteenth Day of September, 2009

David J. Kappos
*Director of the United States Patent and Trademark Office*